(12) United States Patent
Silverman et al.

(10) Patent No.: US 10,196,384 B2
(45) Date of Patent: Feb. 5, 2019

(54) DEUTERATED CFTR MODULATORS

(71) Applicant: VERTEX PHARMACEUTICALS (EUROPE) LIMITED, London (GB)

(72) Inventors: I. Robert Silverman, Arlington, MA (US); Roger D. Tung, Lexington, MA (US)

(73) Assignee: Vertex Pharmaceuticals (Europe) Limited, London (GB)

( * ) Notice: Subject to any disclaimer, the term of this patent is extended or adjusted under 35 U.S.C. 154(b) by 0 days.

(21) Appl. No.: 15/562,860

(22) PCT Filed: Mar. 30, 2016

(86) PCT No.: PCT/US2016/024949
§ 371 (c)(1),
(2) Date: Sep. 28, 2017

(87) PCT Pub. No.: WO2016/160945
PCT Pub. Date: Oct. 6, 2016

(65) Prior Publication Data
US 2018/0111920 A1    Apr. 26, 2018

Related U.S. Application Data

(60) Provisional application No. 62/140,869, filed on Mar. 31, 2015.

(51) Int. Cl.
C07D 405/12    (2006.01)
A61P 11/00    (2006.01)
C07B 59/00    (2006.01)

(52) U.S. Cl.
CPC ............ *C07D 405/12* (2013.01); *A61P 11/00* (2018.01); *C07B 59/002* (2013.01)

(58) Field of Classification Search
None
See application file for complete search history.

(56) References Cited

U.S. PATENT DOCUMENTS

| | | |
|---|---|---|
| 5,846,514 A | 12/1998 | Foster et al. |
| 6,221,335 B1 | 4/2001 | Foster |
| 6,440,710 B1 | 8/2002 | Keinan et al. |
| 6,603,008 B1 | 8/2003 | Ando et al. |
| 7,517,990 B2 | 4/2009 | Ito et al. |
| 7,645,789 B2 | 1/2010 | Hadida Ruah et al. |
| 7,776,905 B2 | 8/2010 | Hadida Ruah et al. |
| 8,415,387 B2 | 4/2013 | Ruah et al. |
| 8,563,573 B2 | 10/2013 | Ruah et al. |
| 8,563,593 B2 | 10/2013 | Alargova et al. |
| 8,575,209 B2 | 11/2013 | Ruah et al. |
| 8,598,181 B2 | 12/2013 | Hadida Ruah et al. |
| 8,623,905 B2 | 1/2014 | Ruah et al. |
| 8,802,868 B2 | 8/2014 | Keshavarz-Shokri et al. |
| 8,865,902 B2 | 10/2014 | Morgan |
| 8,912,199 B2 | 12/2014 | Hadida Ruah et al. |
| 8,952,049 B2 | 2/2015 | Ruah et al. |
| 8,952,050 B2 | 2/2015 | Ruah et al. |
| 9,012,496 B2 | 4/2015 | Alargova et al. |
| 9,035,072 B2 | 5/2015 | Belmont et al. |
| 9,051,303 B2 | 6/2015 | Keshavarz-Shokri et al. |
| 9,102,672 B2 | 8/2015 | Hadida-Ruah et al. |
| 9,181,192 B2 | 11/2015 | Morgan |
| 9,254,291 B2 | 2/2016 | Looker et al. |
| 9,512,079 B2 | 12/2016 | Morgan |
| 9,732,080 B2 | 8/2017 | Hadida-Ruah et al. |
| 9,758,510 B2 | 9/2017 | Hadida Ruah et al. |
| 2007/0082929 A1 | 4/2007 | Gant et al. |
| 2008/0103122 A1 | 5/2008 | Veltri |
| 2011/0251253 A1 | 10/2011 | Keshavarz-Shokri et al. |
| 2012/0046330 A1 | 2/2012 | Alargova et al. |
| 2013/0116238 A1* | 5/2013 | Looker ............... A61K 31/553 514/211.12 |
| 2013/0143919 A1 | 6/2013 | Van Goor et al. |
| 2014/0094499 A1 | 4/2014 | Alargova et al. |
| 2015/0080431 A1 | 3/2015 | Van Goor et al. |
| 2015/0094304 A1 | 4/2015 | Ruah et al. |
| 2015/0119441 A1 | 4/2015 | Hadida Ruah et al. |
| 2015/0174098 A1 | 6/2015 | Ruah et al. |
| 2015/0182517 A1 | 7/2015 | Alargova et al. |
| 2015/0203478 A1 | 7/2015 | Keshavarz-Shokri et al. |
| 2015/0218122 A1 | 8/2015 | Tanoury et al. |
| 2015/0320736 A1 | 11/2015 | Phenix et al. |
| 2016/0067239 A9 | 3/2016 | Van Goor et al. |
| 2016/0166540 A1 | 6/2016 | Looker et al. |

(Continued)

FOREIGN PATENT DOCUMENTS

| | | |
|---|---|---|
| CN | 1148843 A | 4/1997 |
| CN | 101765582 A | 6/2010 |

(Continued)

OTHER PUBLICATIONS

Baillie, T. A. (1981) "The Use of Stable Isotopes in Pharmacological Research" *Pharmacological Reviews*, 33(2):81-132.
Blake, M.I. et al. (1975) "Studies with Deuterated Drugs" *J Pharm Sci*, 64(3):367-391.
Browne, T. R. (1998) "Stable Isotope Techniques in Early Drug Development: An Economic Evaluation" *J Clin Pharmacol*, 38: 213-220.
Buteau, K.C. (Jan. 2009) "Deuterated Drugs: Unexpectedly Nonobvious?" *Journal of High Technology Law*, 10(1):22-74.
Cherrah, Y. et al. (1987) "Study of Deuterium Isotope Effects on Protein Binding by Gas Chromatography/Mass Spectrometry. Caffeine and Deuterated Isotopomers" *Biomedical and Environmental Mass Spectrometry*, 14: 653-657.
Concert Pharmaceuticals, Inc. (2007) "Precision Deuterium Chemistry Backgrounder" [online]. Retrieved from the Internet: URL:http://www.webcitation.org/5e81SGCnI [retrieved on May 12, 2011] (6 pages).

(Continued)

*Primary Examiner* — Samantha L Shterengarts
(74) *Attorney, Agent, or Firm* — Finnegan, Henderson, Farabow, Garrett & Dunner LLP

(57) ABSTRACT

This invention relates to novel, deuterated forms of VX-661 and pharmaceutically acceptable salts thereof. This invention also provides compositions comprising a compound of this invention and the use of such compositions in methods of treating cystic fibrosis.

29 Claims, No Drawings

(56) References Cited

U.S. PATENT DOCUMENTS

| | | |
|---|---|---|
| 2016/0271105 A1 | 9/2016 | Hadida Ruah et al. |
| 2017/0137383 A1 | 5/2017 | Morgan |
| 2017/0189389 A1 | 7/2017 | Hadida-Ruah et al. |
| 2017/0266176 A1 | 9/2017 | Alargova et al. |
| 2018/0086711 A1 | 3/2018 | Morgan |

FOREIGN PATENT DOCUMENTS

| | | |
|---|---|---|
| CN | 102234275 A | 11/2011 |
| JP | H09-510717 A | 10/1997 |
| JP | 2010-539166 A | 12/2010 |
| WO | WO 95/26325 A2 | 10/1995 |
| WO | WO 2003/084954 A1 | 10/2003 |
| WO | WO 2004/000854 A1 | 12/2003 |
| WO | WO 2007/079139 A2 | 7/2007 |
| WO | WO 2007/118651 A1 | 10/2007 |
| WO | WO 2008/134525 A1 | 11/2008 |
| WO | WO 2009/035652 A1 | 3/2009 |
| WO | WO 2010/028015 A2 | 3/2010 |
| WO | WO 2010/053471 A1 | 5/2010 |
| WO | WO 2010/054138 A2 | 5/2010 |
| WO | WO 2011/116397 A1 | 9/2011 |
| WO | WO 2012/158885 A1 | 11/2012 |
| WO | WO 2014/078842 A1 | 5/2014 |
| WO | WO 2016/109362 A1 | 7/2016 |
| WO | WO 2017/053455 A1 | 3/2017 |
| WO | WO 2017/053711 A2 | 3/2017 |

OTHER PUBLICATIONS

Database PUBCHEM, Substance Record for SID 163435970. Create Date: Jun. 10, 2013. [retrieved on Oct. 24, 2016]. Retrieved from the Internet: https://pubchem.ncbi.nlm.nih.gov/substance/1634359070.

Dumont et al. (1982) "Perspectives dans l'utilisation de molécules deutériées en tant qu'agents thérapeutiques (Prospects in the use of deuterated molecules as therapeutic agents)" Revue IRE Tijdschrift, 6(4):2-10 (French).

Dyck, L. E. et al. (1986) "Effects of Deuterium Substitution on the Catabolism of β-Phenylethylamine: An in Vivo Study" *J Neurochem*, 46(2): 399-404.

Fisher, M.B. et al. (2006) "The complexities inherent in attempts to decrease drug clearance by blocking sites of CYP-mediated metabolism" *Curr Opin Drug Disc Develop*, 9(1):101-109.

Foster, A.B. (1984) "Deuterium Isotope Effects in Studies of Drug Metabolism" *Trends in Pharmacological Sciences*, 5:524-527.

Foster, A.B. (Jan. 1985) "Deuterium isotope effects in the metabolism of drugs and xenobiotics: implications for drug design" *Adv Drug Res*, 14:1-40.

Fukuto, J.M. et al. (1991) "Determination of the Mechanism of Demethylenation of (Methylenedioxy)phenyl Compounds by Cytochrome P450 Using Deuterium Isotope Effects" *J Med Chem*, 34:2871-2876.

Gouyette, A. (1988) "Synthesis of Deuterium-labelled Elliptinium and its Use in Metabolic Studies" *Biomedical and Environmental Mass Spectrometry*, 15:243-247.

Haskins, N. J. (1982) "The Application of Stable Isotopes in Biomedical Research" *Biomedical Mass Spectrometry*, 9(7): 269-277.

Honma, S. et al. (1987) "The metabolism of roxatidine acetate hydrochloride. Liberation of deuterium from the piperidine ring during hydroxylation" *Drug Metabolism and Disposition*, 15(4):551-559.

International Search Report and Written Opinion dated Jun. 10, 2016 in International Patent Application No. PCT/US2016/024949, filed Mar. 30, 2016, by Concert Pharmaceuticals, Inc.

Kushner, D.J. et al. (Feb. 1999) "Pharmacological uses and perspectives of heavy water and deuterated compounds" *Canadian J Physiol Pharmacol*, 77(2):79-88.

O'Driscoll, C. (Mar. 9, 2009) "Heavyweight Drugs. Swapping Selected Hydrogen Atoms for Deuterium Could Be a Fast Route to Making Safer, Longer Lasting Drugs" *Chemistry & Industry*, pp. 24-26.

Pieniaszek, H.J. et al. (1999) "Moricizine Bioavailability via Simultaneous, Dual, Stable Isotope Administration: Bioequivalence Implications" *J Clin Pharmacol*, 39:817-825.

Sanderson, K. (2009) "Big interest in heavy drugs. The drug industry is seeking profits by modifying hydrogen in existing medications" *Nature*, 458:269.

U.S. Appl. No. 15/643,182, filed Jul. 6, 2017, by Frederick F. Van Goor, et al.

U.S. Appl. No. 15/793,767, filed Oct. 25, 2017, by Vinita Uttamsingh.

U.S. Appl. No. 15/898,683, filed Feb. 19, 2018, by Frederick F. Van Goor, et al.

U.S. Appl. No. 15/937,564, filed Mar. 27, 2018, by Frederick F. Van Goor, et al.

U.S. Appl. No. 15/949,404, filed Apr. 10, 2018, by Sara Sabina Hadida Ruah, et al.

Wang, Shizhen (Ed.) "Use of Nuclear Technology in Drug Study" Chapter 21 in: *Molecular Nuclear Medicine*. 1st Ed. Beijing, China: Peking Union Medical College Press, Apr. 30, 2004; pp. 416-418 (Chinese).

Wolen, R.L. (1986) "The Application of Stable Isotopes to Studies of Drug Bioavailability and Bioequivalence" *J Clin Pharmacol*, 26:419-424.

\* cited by examiner

DEUTERATED CFTR MODULATORS

CROSS REFERENCE TO RELATED APPLICATIONS

This application is a National Stage Application under 35 U.S.C. § 371 of International Application No. PCT/US2016/024949, filed Mar. 30, 2016, which claims the benefit of U.S. Provisional Application No. 62/140,869, filed Mar. 31, 2015, all of which are incorporated herein by reference.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, AB, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

SUMMARY OF THE INVENTION

This invention relates to novel, deuterated forms of VX-661 and pharmaceutically acceptable salts thereof. This invention also provides compositions comprising a compound of this invention and the use of such compositions in methods of treating cystic fibrosis.

VX-661, also known as 1-(2,2-difluoro-1,3-benzodioxol-5-yl)-N-[1-[2(R),3-dihydroxypropyl]-6-fluoro-2-(1-hydroxy-2-methylpropan-2-yl)-1H-indol-5-yl]cyclopropanecarboxamide, is a deltaF508-cystic fibrosis transmembrane conductance regulator (ΔF508-CFTR) corrector.

VX-661 is currently in phase III human clinical trials for the treatment of cystic fibrosis in patients homozygous for the F508del-CFTR mutation and in phase II clinical trials for the treatment of cystic fibrosis in patients with one copy of the F508del-CFTR mutation and one copy of the G551D CFTR mutation. These CFTR mutations are well-known in the art and are disclosed, e.g., at http://www.genet.sickkids.on.ca/cftr/.

Despite the beneficial activities of VX-661, there is a continuing need for new compounds to treat cystic fibrosis.

DETAILED DESCRIPTION OF THE INVENTION

Definitions

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of VX-661 will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula I, Ia and Ib), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

"Substituted with deuterium" refers to the replacement of one or more hydrogen atoms with a corresponding number of deuterium atoms.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula A:

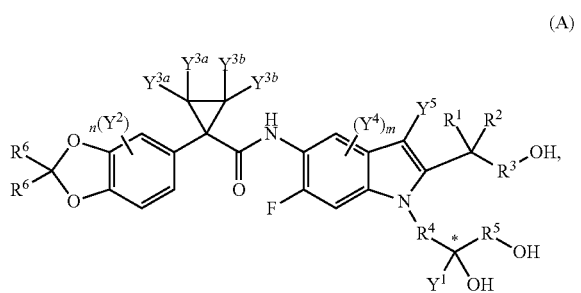

(A)

or a pharmaceutically acceptable salt thereof, wherein:
each of $R^1$ and $R^2$ is independently selected from —$CH_3$, —$CH_2D$, —$CHD_2$, and —$CD_3$;
each of $R^3$, $R^4$ and $R^5$ is independently selected from —$CH_2$—, —CHD- and —$CD_2$-;
each $R^6$ is independently fluorine or deuterium;
$Y^1$ is selected from hydrogen and deuterium;
each $Y^{3a}$ and each $Y^{3b}$ is selected from hydrogen and deuterium;
$Y^5$ is selected from hydrogen and deuterium;
each of $Y^2$ and $Y^4$, if present, is deuterium;
n is 0, 1, 2, or 3;
m is 0, 1, or 2; and
when $R^1$ and $R^2$ are each —$CH_3$; $R^4$, and $R^5$ are each —$CH_2$—; each $R^6$ is fluorine; each $Y^{3a}$ and each $Y^{3b}$ is hydrogen; each of $Y^1$ and $Y^5$ is hydrogen; and each of m and n is 0; then $R^3$ is either —CHD- or —$CD_2$-.

In some embodiments of Formula A, each $R^6$ is fluorine and the compound is a compound of Formula I:

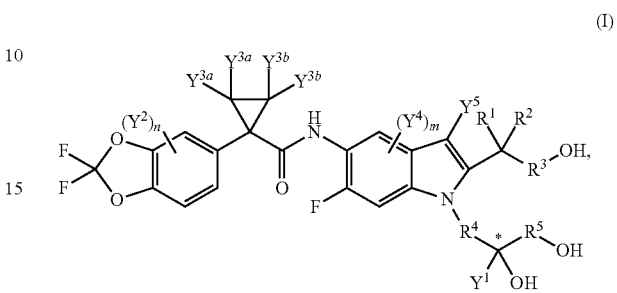

(I)

or a pharmaceutically acceptable salt thereof, wherein:
each of $R^1$ and $R^2$ is independently selected from —$CH_3$, —$CH_2D$, —$CHD_2$, and —$CD_3$;
each of $R^3$, $R^4$ and $R^5$ is independently selected from —$CH_2$—, —CHD- and —$CD_2$-;
$Y^1$ is selected from hydrogen and deuterium;
each $Y^{3a}$ and each $Y^{3b}$ is selected from hydrogen and deuterium;
$Y^5$ is selected from hydrogen and deuterium;
each of $Y^2$ and $Y^4$, if present, is deuterium;
n is 0, 1, 2, or 3;
m is 0, 1, or 2; and
when $R^1$ and $R^2$ are each —$CH_3$; $R^4$, and $R^5$ are each —$CH_2$—; each $Y^{3a}$ and each $Y^{3b}$ is hydrogen; each of $Y^1$ and $Y^5$ is hydrogen; and each of m and n is 0; then $R^3$ is either —CHD- or —$CD_2$-.

In one embodiment, the compound of Formula I is compound of Formula Ia:

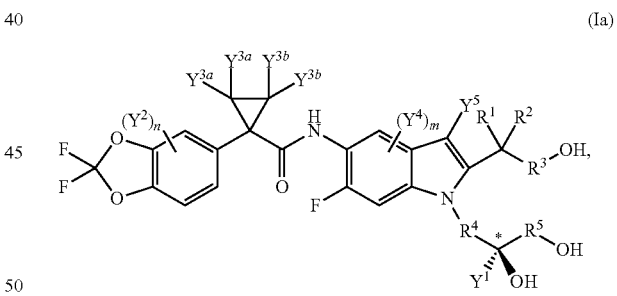

(Ia)

or a pharmaceutically acceptable salt thereof, wherein:
each of $R^1$ and $R^2$ is independently selected from —$CH_3$, —$CH_2D$, —$CHD_2$, and —$CD_3$;
each of $R^3$, $R^4$ and $R^5$ is independently selected from —$CH_2$—, —CHD- and —$CD_2$-;
$Y^1$ is selected from hydrogen and deuterium;
each $Y^{3a}$ and each $Y^{3b}$ is selected from hydrogen and deuterium;
$Y^5$ is selected from hydrogen and deuterium;
each of $Y^2$ and $Y^4$, if present, is deuterium;
n is 0, 1, 2, or 3;
m is 0, 1, or 2; and
when $R^1$ and $R^2$ are each —$CH_3$; $R^4$, and $R^5$ are each —$CH_2$—; each $Y^{3a}$ and each $Y^{3b}$ is hydrogen; each of $Y^1$ and $Y^5$ is hydrogen; and each of m and n is 0; then $R^3$ is either —CHD- or —$CD_2$-.

In one embodiment, the compound of Formula I is a compound of Formula Ib:

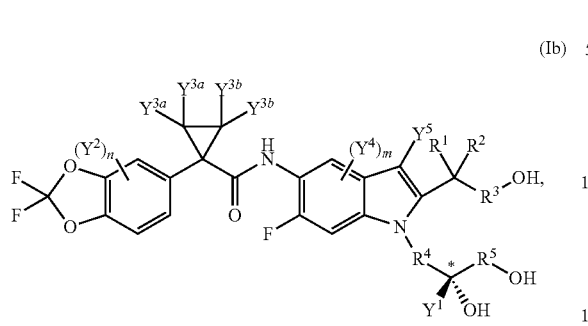

(Ib)

or a pharmaceutically acceptable salt thereof, wherein:
each of $R^1$ and $R^2$ is independently selected from —$CH_3$, —$CH_2D$, —$CHD_2$, and —$CD_3$;
each of $R^3$, $R^4$ and $R^5$ is independently selected from —$CH_2$—, —CHD- and —$CD_2$-;
$Y^1$ is selected from hydrogen and deuterium;
each $Y^{3a}$ and each $Y^{3b}$ is selected from hydrogen and deuterium;
$Y^5$ is selected from hydrogen and deuterium;
each of $Y^2$ and $Y^4$, if present, is deuterium;
n is 0, 1, 2, or 3;
m is 0, 1, or 2; and
when $R^1$ and $R^2$ are each —$CH_3$; $R^4$, and $R^5$ are each —$CH_2$—; each $Y^{3a}$ and each $Y^{3b}$ is hydrogen; each of $Y^1$ and $Y^5$ is hydrogen; and each of m and n is 0; then $R^3$ is either —CHD- or —$CD_2$-.

In some embodiments, each $R^6$ is deuterium and the compound is a compound of Formula II:

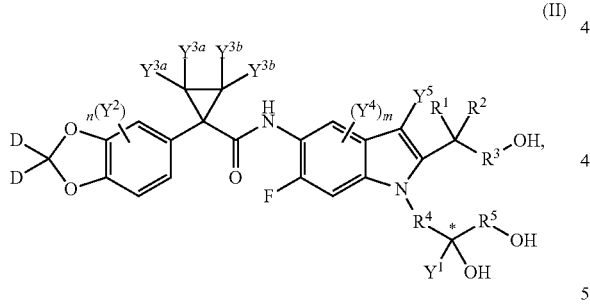

(II)

or a pharmaceutically acceptable salt thereof, wherein:
each of $R^1$ and $R^2$ is independently selected from —$CH_3$, —$CH_2D$, —$CHD_2$, and —$CD_3$;
each of $R^3$, $R^4$ and $R^5$ is independently selected from —$CH_2$—, —CHD- and —$CD_2$-;
$Y^1$ is selected from hydrogen and deuterium;
each $Y^{3a}$ and each $Y^{3b}$ is selected from hydrogen and deuterium;
$Y^5$ is selected from hydrogen and deuterium;
each of $Y^2$ and $Y^4$, if present, is deuterium;
n is 0, 1, 2, or 3; and
m is 0, 1, or 2.

In one embodiment, the compound of Formula II is compound of Formula IIa:

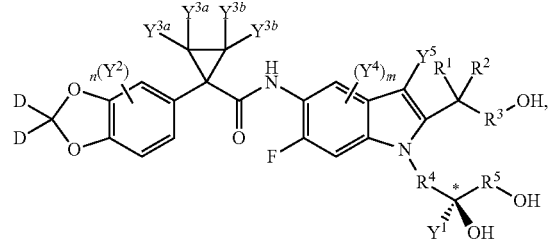

(IIa)

or a pharmaceutically acceptable salt thereof, wherein:
each of $R^1$ and $R^2$ is independently selected from —$CH_3$, —$CH_2D$, —$CHD_2$, and —$CD_3$;
each of $R^3$, $R^4$ and $R^5$ is independently selected from —$CH_2$—, —CHD- and —$CD_2$-;
$Y^1$ is selected from hydrogen and deuterium;
each $Y^{3a}$ and each $Y^{3b}$ is selected from hydrogen and deuterium;
$Y^5$ is selected from hydrogen and deuterium;
each of $Y^2$ and $Y^4$, if present, is deuterium;
n is 0, 1, 2, or 3; and
m is 0, 1, or 2.

In one embodiment, the compound of Formula II is a compound of Formula IIb:

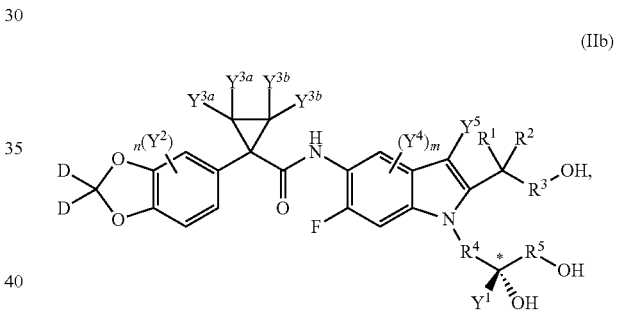

(IIb)

or a pharmaceutically acceptable salt thereof, wherein:
each of $R^1$ and $R^2$ is independently selected from —$CH_3$, —$CH_2D$, —$CHD_2$, and —$CD_3$;
each of $R^3$, $R^4$ and $R^5$ is independently selected from —$CH_2$—, —CHD- and —$CD_2$-;
$Y^1$ is selected from hydrogen and deuterium;
each $Y^{3a}$ and each $Y^{3b}$ is selected from hydrogen and deuterium;
$Y^5$ is selected from hydrogen and deuterium;
each of $Y^2$ and $Y^4$, if present, is deuterium;
n is 0, 1, 2, or 3; and
m is 0, 1, or 2.

The following embodiments pertain to compounds of Formula A, I, Ia, Ib, II, IIa or IIb, where applicable.

In some embodiments $R^1$ is selected from —$CH_3$ and —$CD_3$. In one aspect of these embodiments, $R^1$ is —$CH_3$. In alternate aspects of these embodiments, $R^1$ is —$CD_3$.

In some embodiments $R^2$ is selected from —$CH_3$ and —$CD_3$. In one aspect of these embodiments, $R^2$ is —$CH_3$. In alternate aspects of these embodiments, $R^2$ is —$CD_3$.

In some embodiments $R^3$ is selected from —$CH_2$— and —$CD_2$-. In one aspect of these embodiments, $R^3$ is —$CH_2$—. In alternate aspects of these embodiments, $R^3$ is —$CD_2$-.

In some embodiments $R^4$ is selected from —$CH_2$— and —$CD_2$-. In one aspect of these embodiments, $R^4$ is —$CH_2$—. In alternate aspects of these embodiments, $R^3$ is —$CD_2$-.

In some embodiments $R^5$ is selected from —$CH_2$— and —$CD_2$-. In one aspect of these embodiments, $R^5$ is —$CH_2$—. In alternate aspects of these embodiments, $R^3$ is —$CD_2$-.

In some embodiments, each $R^6$ is the same. In some aspects of these embodiments, each $R^6$ is fluorine. In other aspects of these embodiments, each $R^6$ is deuterium. In more specific aspects of these embodiments, each $R^6$ is deuterium, $R^1$ and $R^2$ are each —$CH_3$; and $R^3$, $R^4$ and $R^5$ are each —$CH_2$—; $Y^1$, each $Y^{3a}$ and each $Y^{3b}$ is hydrogen; and each of m and n is 0.

In some embodiments, n is selected from 0 and 3. In one aspect of these embodiments, n is 0. In an alternate aspect of these embodiments, n is 3.

In some embodiments, m is selected from 0 and 2. In one aspect of these embodiments, m is 2. In an alternate aspect of these embodiments, m is 0.

In some embodiments, m is 0 and $Y^5$ is hydrogen.

In some embodiments, m is 2 and $Y^5$ is deuterium.

In some embodiments each $Y^{3a}$ is the same, and each $Y^{3b}$ is the same. In one aspect of these embodiments, each $Y^{3a}$ and each $Y^{3b}$ is hydrogen. In one aspect of these embodiments, each $Y^{3a}$ and each $Y^{3b}$ is deuterium. In one aspect of these embodiments, each $Y^{3a}$ is hydrogen and each $Y^{3b}$ is deuterium. In one aspect of these embodiments, each $Y^{3a}$ is deuterium and each $Y^{3b}$ is hydrogen.

In some embodiments, each of $Y^{3a}$ and $Y^{3b}$ is hydrogen; $Y^5$ is hydrogen; m is 0 and n is 0. In some aspects of these embodiments, $R^3$ is —$CD_2$-. In other aspects of these embodiments, $R^1$ and $R^2$ are each —$CD_3$ and $R^3$ is —$CD_2$-. In other aspects of these embodiments, $R^1$ and $R^2$ are each —$CD_3$; and $R^3$, $R^4$ and $R^5$ are each —$CD_2$-. In other aspects of these embodiments, $R^4$ and $R^5$ are each —$CD_2$-; and $Y^1$ is deuterium. In still other aspects of these embodiments, $R^1$ and $R^2$ are each —$CD_3$; and $R^3$, $R^4$ and $R^5$ are each —$CD_2$-; and $Y^1$ is deuterium.

In some embodiments, each of $Y^{3a}$ and $Y^{3b}$ is deuterium; $Y^5$ is hydrogen; m is 0 and n is 0. In some aspects of these embodiments, $R^3$ is —$CD_2$-. In other aspects of these embodiments, $R^1$ and $R^2$ are each —$CD_3$ and $R^3$ is —$CD_2$-. In other aspects of these embodiments, $R^1$ and $R^2$ are each —$CD_3$; and $R^3$, $R^4$ and $R^5$ are each —$CD_2$-. In other aspects of these embodiments, $R^4$ and $R^5$ are each —$CD_2$-; and $Y^1$ is deuterium. In still other aspects of these embodiments, $R^1$ and $R^2$ are each —$CD_3$; and $R^3$, $R^4$ and $R^5$ are each —$CD_2$-; and $Y^1$ is deuterium.

In some embodiments, $R^1$ and $R^2$ are independently selected from —$CH_3$ and —$CD_3$; $R^3$, $R^4$ and $R^5$ are independently selected from —$CH_2$— and —$CD_2$-; each of $Y^{3a}$ and $Y^{3b}$ is hydrogen; $Y^5$ is hydrogen; m is 0 and n is 0. In one aspect of these embodiments, $R^1$ and $R^2$ are each —$CD_3$; and $R^3$, $R^4$ and $R^5$ are each —$CD_2$-.

In some embodiments, $R^1$ and $R^2$ are the same and each is selected from —$CH_3$ and —$CD_3$. In one aspect of these embodiments, $R^1$ and $R^2$ are each —$CH_3$. In another aspect of these embodiments, $R^1$ and $R^2$ are each —$CD_3$. In another aspect of these embodiments, $R^3$ is —$CD_2$- when $R^1$ and $R^2$ are each —$CD_3$. In an alternate aspect of these embodiments $R^3$ is —$CH_2$ when $R^1$ and $R^2$ are each —$CH_3$. In another aspect of these embodiments, $R^3$ is —$CD_2$- when $R^1$ and $R^2$ are each —$CH_3$. In an alternate aspect of these embodiments $R^3$ is —$CH_2$— when $R^1$ and $R^2$ are each —$CD_3$.

In some embodiments, $R^1$ and $R^2$ are different from one another and each is independently selected from —$CH_3$ and —$CD_3$. In one aspect of these embodiments, $R^1$ is —$CD_3$; and $R^2$ is —$CH_3$. In another aspect of these embodiments, $R^1$ is —$CH_3$; and $R^2$ is —$CD_3$. In another aspect of these embodiments, $R^3$ is —$CD_2$- when $R^1$ is —$CH_3$; and $R^2$ is —$CD_3$. In yet another aspect of these embodiments, $R^3$ is —$CD_2$- when $R^1$ is —$CD_3$; and $R^2$ is —$CH_3$. In an alternate aspect of these embodiments $R^3$ is —$CH_2$— when $R^1$ is —$CH_3$; and $R^2$ is —$CD_3$. In yet another aspect of these embodiments, $R^3$ is —$CH_2$— when $R^1$ is —$CD_3$; and $R^2$ is —$CH_3$.

In some embodiments, $R^4$ and $R^5$ are the same and each is selected from —$CH_2$— and —$CD_2$-. In one aspect of these embodiments, $R^4$ and $R^5$ are each —$CH_2$—. In another aspect of these embodiments, $R^4$ and $R^5$ are each —$CD_2$-. In another aspect of these embodiments, $Y^1$ is deuterium when $R^4$ and $R^5$ are each —$CD_2$-. In an alternate aspect of these embodiments, $Y^1$ is deuterium when $R^4$ and $R^5$ are each —$CH_2$—. In an alternate aspect of these embodiments, $Y^1$ is hydrogen when $R^4$ and $R^5$ are each —$CH_2$—. In an alternate aspect of these embodiments, $Y^1$ is hydrogen when $R^4$ and $R^5$ are each —$CD_2$-.

In some embodiments, one of $R^4$ and $R^5$ is —$CH_2$— and the other is —$CD_2$-. In one aspect of these embodiments, $R^4$ is —$CD_2$-; and $R^5$ is —$CH_2$—. In another aspect of these embodiments, $R^4$ is —$CH_2$—; and $R^5$ is —$CD_2$-. In another aspect of these embodiments, $Y^1$ is deuterium; $R^4$ is —$CH_2$—; and $R^5$ is —$CD_2$-. In an alternate aspect of these embodiments, $Y^1$ is deuterium; $R^4$ is —$CD_2$-; and $R^5$ is —$CH_2$—. In another aspect of these embodiments, $Y^1$ is hydrogen; $R^4$ is —$CH_2$—; and $R^5$ is —$CD_2$-. In an alternate aspect of these embodiments, $Y^1$ is hydrogen; $R^4$ is —$CD_2$- and $R^5$ is —$CH_2$—.

In some embodiments, $R^1$ and $R^2$ are each —$CD_3$; $R^3$ is —$CD_2$-; $R^4$ and $R^5$ are each —$CD_2$- and $Y^1$ is deuterium.

In some embodiments, $R^1$ and $R^2$ are each —$CD_3$; $R^3$ is —$CD_2$-; $R^4$ and $R^5$ are each —$CH_2$— and $Y^1$ is hydrogen.

In some embodiments, $R^1$ and $R^2$ are each —$CD_3$; $R^3$ is —$CD_2$-; $R^4$ and $R^5$ are each —$CD_2$ and $Y^1$ is hydrogen.

In some embodiments, $R^1$ and $R^2$ are each —$CD_3$; $R^3$ is —$CD_2$; $R^4$ and $R^5$ are each —$CH_2$— and $Y^1$ is deuterium.

In some embodiments, $R^1$ and $R^2$ are each —$CD_3$; $R^3$ is —$CD_2$-; $R^4$ is —$CH_2$—; $R^5$ is —$CD_2$- and $Y^1$ is deuterium.

In some embodiments, $R^1$ and $R^2$ are each —$CD_3$; $R^3$ is —$CD_2$-; $R^4$ is —$CD_2$-; $R^5$ is —$CH_2$— and $Y^1$ is deuterium.

In some embodiments, $R^1$ and $R^2$ are each —$CD_3$; $R^3$ is —$CD_2$-; $R^4$ is —$CH_2$—; $R^5$ is —$CD_2$- and $Y^1$ is hydrogen.

In some embodiments, $R^1$ and $R^2$ are each —$CD_3$; $R^3$ is —$CD_2$-; $R^4$ is —$CD_2$-; $R^5$ is —$CH_2$— and $Y^1$ is hydrogen.

In some embodiments, $R^1$ and $R^2$ are each —$CH_3$; $R^3$ is —$CH_2$—; $R^4$ and $R^5$ are each —$CD_2$- and $Y^1$ is deuterium.

In some embodiments, $R^1$ and $R^2$ are each —$CH_3$; $R^3$ is —$CH_2$—; $R^4$ and $R^5$ are each —$CD_2$- and $Y^1$ is hydrogen.

In some embodiments, $R^1$ and $R^2$ are each —$CH_3$; $R^3$ is —$CH_2$—; $R^4$ and $R^5$ are each —$CH_2$— and $Y^1$ is deuterium.

In some embodiments, $R^1$ and $R^2$ are each —$CH_3$; $R^3$ is —$CH_2$—; $R^4$ is —$CH_2$—; $R^5$ is —$CD_2$- and $Y^1$ is deuterium.

In some embodiments, $R^1$ and $R^2$ are each —$CH_3$; $R^3$ is —$CH_2$—; $R^4$ is —$CD_2$-; $R^5$ is —$CH_2$— and $Y^1$ is deuterium.

In some embodiments, $R^1$ and $R^2$ are each —$CH_3$; $R^3$ is —$CH_2$; $R^4$ is —$CH_2$; $R^5$ is —$CD_2$ and $Y^1$ is hydrogen.

In some embodiments, $R^1$ and $R^2$ are each —$CH_3$; $R^3$ is —$CH_2$—; $R^4$ is —$CD_2$-; $R^5$ is —$CH_2$— and $Y^1$ is hydrogen.

In some embodiments, $R^1$ and $R^2$ are each —$CD_3$; $R^3$ is —$CH_2$—; $R^4$ and $R^5$ are each —$CD_2$- and $Y^1$ is deuterium.

In some embodiments, $R^1$ and $R^2$ are each —$CD_3$; $R^3$ is —$CH_2$—; $R^4$ and $R^5$ are each —$CH_2$— and $Y^1$ is hydrogen.

In some embodiments, $R^1$ and $R^2$ are each —$CD_3$; $R^3$ is —$CH_2$—; $R^4$ and $R^5$ are each —$CD_2$- and $Y^1$ is hydrogen.

In some embodiments, $R^1$ and $R^2$ are each —$CD_3$; $R^3$ is —$CH_2$—; $R^4$ and $R^5$ are each —$CH_2$— and $Y^1$ is deuterium.

In some embodiments, $R^1$ and $R^2$ are each —$CD_3$; $R^3$ is —$CH_2$—; $R^4$ is —$CH_2$—; $R^5$ is —$CD_2$- and $Y^1$ is deuterium.

In some embodiments, $R^1$ and $R^2$ are each —$CD_3$; $R^3$ is —$CH_2$—; $R^4$ is —$CD_2$-; $R^5$ is —$CH_2$— and $Y^1$ is deuterium.

In some embodiments, $R^1$ and $R^2$ are each —$CD_3$; $R^3$ is —$CH_2$—; $R^4$ is —$CH_2$—; $R^5$ is —$CD_2$- and $Y^1$ is hydrogen.

In some embodiments, $R^1$ and $R^2$ are each —$CD_3$; $R^3$ is —$CH_2$—; $R^4$ is —$CD_2$-; $R^5$ is —$CH_2$— and $Y^1$ is hydrogen.

In some embodiments, $R^1$ and $R^2$ are each —$CH_3$; $R^3$ is —$CD_2$-; $R^4$ and $R^5$ are each —$CD_2$- and $Y^1$ is deuterium.

In some embodiments, $R^1$ and $R^2$ are each —$CH_3$; $R^3$ is —$CD_2$-; $R^4$ and $R^5$ are each —$CD_2$- and $Y^1$ is hydrogen.

In some embodiments, $R^1$ and $R^2$ are each —$CH_3$; $R^3$ is —$CD_2$-; $R^4$ and $R^5$ are each —$CH_2$— and $Y^1$ is deuterium.

In some embodiments, $R^1$ and $R^2$ are each —$CH_3$; $R^3$ is —$CD_2$-; $R^4$ and $R^5$ are each —$CH_2$— and $Y^1$ is hydrogen.

In some embodiments, $R^1$ and $R^2$ are each —$CH_3$; $R^3$ is —$CD_2$-; $R^4$ is —$CH_2$—; $R^5$ is —$CD_2$- and $Y^1$ is deuterium.

In some embodiments, $R^1$ and $R^2$ are each —$CH_3$; $R^3$ is —$CD_2$-; $R^4$ is —$CD_2$-; $R^5$ is —$CH_2$— and $Y^1$ is deuterium.

In some embodiments, $R^1$ and $R^2$ are each —$CH_3$; $R^3$ is —$CD_2$-; $R^4$ is —$CH_2$—; $R^5$ is —$CD_2$- and $Y^1$ is hydrogen.

In some embodiments, $R^1$ and $R^2$ are each —$CH_3$; $R^3$ is —$CD_2$-; $R^4$ is —$CD_2$-; $R^5$ is —$CH_2$— and $Y^1$ is hydrogen.

In some embodiments, $R^1$ is —$CH_3$; $R^2$ is —$CD_3$; $R^3$ is —$CH_2$—; $R^4$ and $R^5$ are each —$CD_2$- and $Y^1$ is deuterium.

In some embodiments, $R^1$ is —$CH_3$; $R^2$ is —$CD_3$; $R^3$ is —$CH_2$—; $R^4$ and $R^5$ are each —$CH_2$— and $Y^1$ is hydrogen.

In some embodiments, $R^1$ is —$CH_3$; $R^2$ is —$CD_3$; $R^3$ is —$CH_2$—; $R^4$ and $R^5$ are each —$CD_2$- and $Y^1$ is hydrogen.

In some embodiments, $R^1$ is —$CH_3$; $R^2$ is —$CD_3$; $R^3$ is —$CH_2$—; $R^4$ and $R^5$ are each —$CH_2$— and $Y^1$ is deuterium.

In some embodiments, $R^1$ is —$CH_3$; $R^2$ is —$CD_3$; $R^3$ is —$CH_2$—; $R^4$ is —$CH_2$—; $R^5$ is —$CD_2$- and $Y^1$ is deuterium.

In some embodiments, $R^1$ is —$CH_3$; $R^2$ is —$CD_3$; $R^3$ is —$CH_2$—; $R^4$ is —$CD_2$-; $R^5$ is —$CH_2$— and $Y^1$ is deuterium.

In some embodiments, $R^1$ is —$CH_3$; $R^2$ is —$CD_3$; $R^3$ is —$CH_2$—; $R^4$ is —$CH_2$—; $R^5$ is —$CD_2$- and $Y^1$ is hydrogen.

In some embodiments, $R^1$ is —$CH_3$; $R^2$ is —$CD_3$; $R^3$ is —$CH_2$—; $R^4$ is —$CD_2$-; $R^5$ is —$CH_2$— and $Y^1$ is hydrogen.

In some embodiments, $R^1$ is —$CD_3$; $R^2$ is —$CH_3$; $R^3$ is —$CD_2$-; $R^4$ and $R^5$ are each —$CD_2$- and $Y^1$ is deuterium.

In some embodiments, $R^1$ is —$CD_3$; $R^2$ is —$CH_3$; $R^3$ is —$CD_2$-; $R^4$ and $R^5$ are each —$CD_2$- and $Y^1$ is hydrogen.

In some embodiments, $R^1$ is —$CD_3$; $R^2$ is —$CH_3$; $R^3$ is —$CD_2$-; $R^4$ and $R^5$ are each —$CH_2$— and $Y^1$ is deuterium.

In some embodiments, $R^1$ is —$CD_3$; $R^2$ is —$CH_3$; $R^3$ is —$CD_2$- $R^4$ and $R^5$ are each —$CH_2$— and $Y^1$ is hydrogen.

In some embodiments, $R^1$ is —$CD_3$; $R^2$ is —$CH_3$; $R^3$ is —$CD_2$-; $R^4$ is —$CH$—; $R^5$ is —$CD_2$- and $Y^1$ is deuterium.

In some embodiments, $R^1$ is —$CD_3$; $R^2$ is —$CH_3$; $R^3$ is —$CD_2$-; $R^4$ is —$CD_2$-; $R^5$ is —$CH_2$— and $Y^1$ is deuterium.

In some embodiments, $R^1$ is —$CD_3$; $R^2$ is —$CH_3$; $R^3$ is —$CD_2$-; $R^4$ is —$CH$—; $R^5$ is —$CD_2$- and $Y^1$ is hydrogen.

In some embodiments, $R^1$ is —$CD_3$; $R^2$ is —$CH_3$; $R^3$ is —$CD_2$-; $R^4$ is —$CD_2$-; $R^5$ is —$CH_2$— and $Y^1$ is hydrogen.

In some embodiments, when $R^1$ is —$CH_3$; $R^2$ is —$CH_3$; $R^3$ is —$CH$—; $R^4$ is —$CH$—;

$R^5$ is —$CH_2$— and $Y^1$ is hydrogen, at least one of $Y^2$, $Y^{3a}$, $Y^{3b}$, $Y^4$ and $Y^5$ is deuterium.

In some embodiments, when $R^1$ is —$CH_3$; $R^2$ is —$CH_3$; $R^3$ is —$CH$—; $R^4$ is —$CH_2$—; $R^5$ is —$CH_2$— and $Y^1$ is hydrogen, at least one of $Y^{3a}$, $Y^{3b}$, and $Y^5$ is deuterium or either n or m is not 0.

In some embodiments of this invention, a compound of Formula A does not include a compound wherein each of $R^1$ and $R^2$ is —$CD_3$; each of $R^3$, $R^4$ and $R^5$ is —$CD_2$-; each $R^6$ is fluorine; $Y^1$ is deuterium; each $Y^{3a}$ and each $Y^{3b}$ is deuterium; $Y^5$ is deuterium; n is 3; and m is 2.

In some embodiments of this invention, a compound of Formula I, Ia or Ib does not include a compound wherein each of $R^1$ and $R^2$ is —$CD_3$; each of $R^3$, $R^4$ and $R^5$ is —$CD_2$-; $Y^1$ is deuterium; each $Y^{3a}$ and each $Y^{3b}$ is deuterium; $Y^5$ is deuterium; n is 3; and m is 2.

In one embodiment of a compound of Formula I, $R^1$ and $R^2$ are the same; each of m and n is 0; $Y^5$ is hydrogen; each $Y^{3a}$ and $Y^{3b}$ is hydrogen; and the compound is selected from any one of the compounds set forth in Table 1a (below):

TABLE 1a

Exemplary Embodiments of Formula I

| Compound # | $R^1/R^2$ | $R^3$ | $R^4$ | $R^5$ | $Y^1$ |
|---|---|---|---|---|---|
| 100 | $CD_3$ | $CD_2$ | $CD_2$ | $CH_2$ | H |
| 101 | $CD_3$ | $CD_2$ | $CD_2$ | $CD_2$ | H |
| 102 | $CD_3$ | $CD_2$ | $CH_2$ | $CH_2$ | H |
| 103 | $CD_3$ | $CD_2$ | $CH_2$ | $CD_2$ | H |
| 104 | $CD_3$ | $CD_2$ | $CD_2$ | $CH_2$ | D |
| 105 | $CD_3$ | $CD_2$ | $CD_2$ | $CD_2$ | D |
| 106 | $CD_3$ | $CD_2$ | $CH_2$ | $CH_2$ | D |
| 107 | $CD_3$ | $CD_2$ | $CH_2$ | $CD_2$ | D |
| 108 | $CH_3$ | $CH_2$ | $CD_2$ | $CH_2$ | H |
| 109 | $CH_3$ | $CH_2$ | $CD_2$ | $CD_2$ | H |
| 110 | $CH_3$ | $CH_2$ | $CH_2$ | $CD_2$ | H |
| 111 | $CH_3$ | $CH_2$ | $CD_2$ | $CH_2$ | D |
| 112 | $CH_3$ | $CH_2$ | $CD_2$ | $CD_2$ | D |
| 113 | $CH_3$ | $CH_2$ | $CH_2$ | $CH_2$ | D |
| 114 | $CH_3$ | $CH_2$ | $CH_2$ | $CD_2$ | D |
| 115 | $CD_3$ | $CH_2$ | $CD_2$ | $CH_2$ | H |
| 116 | $CD_3$ | $CH_2$ | $CD_2$ | $CD_2$ | H |
| 117 | $CD_3$ | $CH_2$ | $CH_2$ | $CH_2$ | H |
| 118 | $CD_3$ | $CH_2$ | $CH_2$ | $CD_2$ | H |
| 119 | $CD_3$ | $CH_2$ | $CD_2$ | $CH_2$ | D |
| 120 | $CD_3$ | $CH_2$ | $CD_2$ | $CD_2$ | D |
| 121 | $CD_3$ | $CH_2$ | $CH_2$ | $CH_2$ | D |
| 122 | $CD_3$ | $CH_2$ | $CH_2$ | $CD_2$ | D |
| 123 | $CH_3$ | $CD_2$ | $CD_2$ | $CH_2$ | H |
| 124 | $CH_3$ | $CD_2$ | $CD_2$ | $CD_2$ | H |
| 125 | $CH_3$ | $CD_2$ | $CH_2$ | $CD_2$ | H |
| 126 | $CH_3$ | $CD_2$ | $CH_2$ | $CH_2$ | H |
| 127 | $CH_3$ | $CD_2$ | $CD_2$ | $CH_2$ | D |
| 128 | $CH_3$ | $CD_2$ | $CD_2$ | $CD_2$ | D |
| 129 | $CH_3$ | $CD_2$ | $CH_2$ | $CH_2$ | D |
| 130 | $CH_3$ | $CD_2$ | $CH_2$ | $CD_2$ | D | or a pharmaceutically acceptable salt thereof.

In one embodiment of a compound of Formula I, $R^1$ and $R^2$ are the same; each of m and n is 0; $Y^5$ is hydrogen; each $Y^{3a}$ and $Y^{3b}$ is deuterium; and the compound is selected from any one of the compounds set forth in Table 1b (below):

TABLE 1b

Exemplary Embodiments of Formula I

| Compound # | $R^1/R^2$ | $R^3$ | $R^4$ | $R^5$ | $Y^1$ |
|---|---|---|---|---|---|
| 200 | $CD_3$ | $CD_2$ | $CD_2$ | $CH_2$ | H |
| 201 | $CD_3$ | $CD_2$ | $CD_2$ | $CD_2$ | H |
| 202 | $CD_3$ | $CD_2$ | $CH_2$ | $CH_2$ | H |
| 203 | $CD_3$ | $CD_2$ | $CH_2$ | $CD_2$ | H |
| 204 | $CD_3$ | $CD_2$ | $CD_2$ | $CH_2$ | D |
| 205 | $CD_3$ | $CD_2$ | $CD_2$ | $CD_2$ | D |
| 206 | $CD_3$ | $CD_2$ | $CH_2$ | $CH_2$ | D |
| 207 | $CD_3$ | $CD_2$ | $CH_2$ | $CD_2$ | D |
| 208 | $CH_3$ | $CH_2$ | $CD_2$ | $CH_2$ | H |
| 209 | $CH_3$ | $CH_2$ | $CD_2$ | $CD_2$ | H |
| 210 | $CH_3$ | $CH_2$ | $CH_2$ | $CD_2$ | H |
| 211 | $CH_3$ | $CH_2$ | $CD_2$ | $CH_2$ | D |
| 212 | $CH_3$ | $CH_2$ | $CD_2$ | $CD_2$ | D |
| 213 | $CH_3$ | $CH_2$ | $CH_2$ | $CH_2$ | D |
| 214 | $CH_3$ | $CH_2$ | $CH_2$ | $CD_2$ | D |
| 215 | $CH_3$ | $CH_2$ | $CD_2$ | $CH_2$ | H |
| 216 | $CD_3$ | $CH_2$ | $CD_2$ | $CD_2$ | H |
| 217 | $CD_3$ | $CH_2$ | $CD_2$ | $CH_2$ | H |
| 218 | $CD_3$ | $CH_2$ | $CH_2$ | $CD_2$ | H |
| 219 | $CD_3$ | $CH_2$ | $CH_2$ | $CD_2$ | D |
| 220 | $CD_3$ | $CH_2$ | $CD_2$ | $CD_2$ | D |
| 221 | $CD_3$ | $CH_2$ | $CD_2$ | $CH_2$ | D |
| 222 | $CD_3$ | $CH_2$ | $CH_2$ | $CH_2$ | D |
| 223 | $CH_3$ | $CD_2$ | $CD_2$ | $CH_2$ | H |
| 224 | $CH_3$ | $CD_2$ | $CD_2$ | $CD_2$ | H |
| 225 | $CH_3$ | $CD_2$ | $CH_2$ | $CD_2$ | H |
| 226 | $CH_3$ | $CD_2$ | $CH_2$ | $CH_2$ | H |
| 227 | $CH_3$ | $CD_2$ | $CH_2$ | $CD_2$ | D |
| 228 | $CH_3$ | $CD_2$ | $CD_2$ | $CD_2$ | D |
| 229 | $CH_3$ | $CD_2$ | $CH_2$ | $CH_2$ | D |
| 230 | $CH_3$ | $CD_2$ | $CH_2$ | $CD_2$ | D |
| 231 | $CH_3$ | $CH_2$ | $CH_2$ | $CH_2$ | H | or a pharmaceutically acceptable salt thereof.

In one embodiment of a compound of Formula Ia, $R^1$ and $R^2$ are the same; each of m and n is 0; $Y^5$ is hydrogen; each $Y^{3a}$ and $Y^{3b}$ is hydrogen; and the compound is selected from any one of the compounds set forth in Table 2a (below):

TABLE 2a

Exemplary Embodiments of Formula Ia

| Compound # | $R^1/R^2$ | $R^3$ | $R^4$ | $R^5$ | $Y^1$ |
|---|---|---|---|---|---|
| 100a | $CD_3$ | $CD_2$ | $CD_2$ | $CH_2$ | H |
| 101a | $CD_3$ | $CD_2$ | $CD_2$ | $CD_2$ | H |
| 102a | $CD_3$ | $CD_2$ | $CH_2$ | $CH_2$ | H |
| 103a | $CD_3$ | $CD_2$ | $CH_2$ | $CD_2$ | H |
| 104a | $CD_3$ | $CD_2$ | $CD_2$ | $CH_2$ | D |
| 105a | $CD_3$ | $CD_2$ | $CD_2$ | $CD_2$ | D |
| 106a | $CD_3$ | $CD_2$ | $CH_2$ | $CH_2$ | D |
| 107a | $CD_3$ | $CD_2$ | $CH_2$ | $CD_2$ | D |
| 108a | $CH_3$ | $CH_2$ | $CD_2$ | $CH_2$ | H |
| 109a | $CH_3$ | $CH_2$ | $CD_2$ | $CD_2$ | H |
| 110a | $CH_3$ | $CH_2$ | $CH_2$ | $CD_2$ | H |
| 111a | $CH_3$ | $CH_2$ | $CD_2$ | $CH_2$ | D |
| 112a | $CH_3$ | $CH_2$ | $CD_2$ | $CD_2$ | D |
| 113a | $CH_3$ | $CH_2$ | $CH_2$ | $CH_2$ | D |
| 114a | $CH_3$ | $CH_2$ | $CH_2$ | $CD_2$ | D |
| 115a | $CD_3$ | $CH_2$ | $CD_2$ | $CH_2$ | H |
| 116a | $CD_3$ | $CH_2$ | $CD_2$ | $CD_2$ | H |
| 117a | $CD_3$ | $CH_2$ | $CD_2$ | $CH_2$ | H |
| 118a | $CD_3$ | $CH_2$ | $CH_2$ | $CD_2$ | H |
| 119a | $CD_3$ | $CH_2$ | $CH_2$ | $CD_2$ | D |
| 120a | $CD_3$ | $CH_2$ | $CD_2$ | $CD_2$ | D |
| 121a | $CD_3$ | $CH_2$ | $CD_2$ | $CH_2$ | D |
| 122a | $CD_3$ | $CH_2$ | $CH_2$ | $CH_2$ | D |
| 123a | $CH_3$ | $CD_2$ | $CD_2$ | $CH_2$ | D |
| 124a | $CH_3$ | $CD_2$ | $CD_2$ | $CD_2$ | H |
| 125a | $CH_3$ | $CD_2$ | $CH_2$ | $CH_2$ | H |
| 126a | $CH_3$ | $CD_2$ | $CH_2$ | $CH_2$ | H |
| 127a | $CH_3$ | $CD_2$ | $CD_2$ | $CH_2$ | D |
| 128a | $CH_3$ | $CD_2$ | $CD_2$ | $CD_2$ | D |
| 129a | $CH_3$ | $CD_2$ | $CH_2$ | $CH_2$ | D |
| 130a | $CH_3$ | $CD_2$ | $CH_2$ | $CD_2$ | D | or a pharmaceutically acceptable salt thereof.

In one embodiment of a compound of Formula Ia, $R^1$ and $R^2$ are the same; each of m and n is 0; $Y^5$ is hydrogen; each $Y^{3a}$ and $Y^{3b}$ is deuterium; and the compound is selected from any one of the compounds set forth in Table 2b (below):

TABLE 2b

Exemplary Embodiments of Formula Ia

| Compound # | $R^1/R^2$ | $R^3$ | $R^4$ | $R^5$ | $Y^1$ |
|---|---|---|---|---|---|
| 200a | $CD_3$ | $CD_2$ | $CD_2$ | $CH_2$ | H |
| 201a | $CD_3$ | $CD_2$ | $CD_2$ | $CD_2$ | H |
| 202a | $CD_3$ | $CD_2$ | $CH_2$ | $CH_2$ | H |
| 203a | $CD_3$ | $CD_2$ | $CH_2$ | $CD_2$ | H |
| 204a | $CD_3$ | $CD_2$ | $CD_2$ | $CH_2$ | D |
| 205a | $CD_3$ | $CD_2$ | $CD_2$ | $CD_2$ | D |
| 206a | $CD_3$ | $CD_2$ | $CH_2$ | $CH_2$ | D |
| 207a | $CD_3$ | $CD_2$ | $CH_2$ | $CD_2$ | D |
| 208a | $CH_3$ | $CH_2$ | $CD_2$ | $CH_2$ | H |
| 209a | $CH_3$ | $CH_2$ | $CD_2$ | $CD_2$ | H |
| 210a | $CH_3$ | $CH_2$ | $CH_2$ | $CD_2$ | H |
| 211a | $CH_3$ | $CH_2$ | $CD_2$ | $CH_2$ | D |
| 212a | $CH_3$ | $CH_2$ | $CD_2$ | $CD_2$ | D |
| 213a | $CH_3$ | $CH_2$ | $CH_2$ | $CH_2$ | D |
| 214a | $CH_3$ | $CH_2$ | $CH_2$ | $CD_2$ | D |
| 215a | $CD_3$ | $CH_2$ | $CD_2$ | $CH_2$ | H |
| 216a | $CD_3$ | $CH_2$ | $CD_2$ | $CD_2$ | H |
| 217a | $CD_3$ | $CH_2$ | $CD_2$ | $CH_2$ | H |
| 218a | $CD_3$ | $CH_2$ | $CH_2$ | $CD_2$ | H |
| 219a | $CD_3$ | $CH_2$ | $CH_2$ | $CD_2$ | D |
| 220a | $CD_3$ | $CH_2$ | $CD_2$ | $CD_2$ | D |
| 221a | $CD_3$ | $CH_2$ | $CD_2$ | $CH_2$ | D |
| 222a | $CD_3$ | $CH_2$ | $CH_2$ | $CH_2$ | D |
| 223a | $CH_3$ | $CD_2$ | $CD_2$ | $CH_2$ | H |
| 224a | $CH_3$ | $CD_2$ | $CD_2$ | $CD_2$ | H |
| 225a | $CH_3$ | $CD_2$ | $CH_2$ | $CD_2$ | H |
| 226a | $CH_3$ | $CD_2$ | $CH_2$ | $CH_2$ | H |
| 227a | $CH_3$ | $CD_2$ | $CH_2$ | $CD_2$ | D |
| 228a | $CH_3$ | $CD_2$ | $CD_2$ | $CD_2$ | D |
| 229a | $CH_3$ | $CD_2$ | $CH_2$ | $CH_2$ | D |
| 230a | $CH_3$ | $CD_2$ | $CH_2$ | $CD_2$ | D |
| 231a | $CH_3$ | $CH_2$ | $CH_2$ | $CH_2$ | H | or a pharmaceutically acceptable salt thereof.

In one embodiment of a compound of Formula Ib, $R^1$ and $R^2$ are the same; each of m and n is 0; $Y^5$ is hydrogen; each $Y^{3a}$ and $Y^{3b}$ is hydrogen; and the compound is selected from any one of the compounds set forth in Table 3a (below):

TABLE 3a

Exemplary Embodiments of Formula Ib

| Compound # | $R^1/R^2$ | $R^3$ | $R^4$ | $R^5$ | $Y^1$ |
|---|---|---|---|---|---|
| 100b | $CD_3$ | $CD_2$ | $CD_2$ | $CH_2$ | H |
| 101b | $CD_3$ | $CD_2$ | $CD_2$ | $CD_2$ | H |
| 102b | $CD_3$ | $CD_2$ | $CH_2$ | $CH_2$ | H |
| 103b | $CD_3$ | $CD_2$ | $CH_2$ | $CD_2$ | H |
| 104b | $CD_3$ | $CD_2$ | $CD_2$ | $CH_2$ | D |
| 105b | $CD_3$ | $CD_2$ | $CD_2$ | $CD_2$ | D |
| 106b | $CD_3$ | $CD_2$ | $CH_2$ | $CH_2$ | D |
| 107b | $CD_3$ | $CD_2$ | $CH_2$ | $CD_2$ | D |
| 108b | $CH_3$ | $CH_2$ | $CD_2$ | $CH_2$ | H |

TABLE 3a-continued

Exemplary Embodiments of Formula Ib

| Compound # | $R^1/R^2$ | $R^3$ | $R^4$ | $R^5$ | $Y^1$ |
|---|---|---|---|---|---|
| 109b | $CH_3$ | $CH_2$ | $CD_2$ | $CD_2$ | H |
| 110b | $CH_3$ | $CH_2$ | $CH_2$ | $CD_2$ | H |
| 111b | $CH_3$ | $CH_2$ | $CD_2$ | $CH_2$ | D |
| 112b | $CH_3$ | $CH_2$ | $CD_2$ | $CD_2$ | D |
| 113b | $CH_3$ | $CH_2$ | $CH_2$ | $CH_2$ | D |
| 114b | $CH_3$ | $CH_2$ | $CH_2$ | $CD_2$ | D |
| 115b | $CD_3$ | $CH_2$ | $CH_2$ | $CH_2$ | H |
| 116b | $CD_3$ | $CH_2$ | $CD_2$ | $CD_2$ | H |
| 117b | $CD_3$ | $CH_2$ | $CD_2$ | $CH_2$ | H |
| 118b | $CD_3$ | $CH_2$ | $CH_2$ | $CD_2$ | H |
| 119b | $CD_3$ | $CH_2$ | $CD_2$ | $CH_2$ | D |
| 120b | $CD_3$ | $CH_2$ | $CD_2$ | $CD_2$ | D |
| 121b | $CD_3$ | $CH_2$ | $CH_2$ | $CH_2$ | D |
| 122b | $CD_3$ | $CH_2$ | $CH_2$ | $CD_2$ | D |
| 123b | $CH_3$ | $CD_2$ | $CD_2$ | $CH_2$ | H |
| 124b | $CH_3$ | $CD_2$ | $CD_2$ | $CD_2$ | H |
| 125b | $CH_3$ | $CD_2$ | $CH_2$ | $CD_2$ | H |
| 126b | $CH_3$ | $CD_2$ | $CH_2$ | $CH_2$ | H |
| 127b | $CH_3$ | $CD_2$ | $CD_2$ | $CH_2$ | D |
| 128b | $CH_3$ | $CD_2$ | $CD_2$ | $CD_2$ | D |
| 129b | $CH_3$ | $CD_2$ | $CH_2$ | $CH_2$ | D |
| 130b | $CH_3$ | $CD_2$ | $CH_2$ | $CD_2$ | D | or a pharmaceutically acceptable salt thereof.

In one embodiment of a compound of Formula Ib, $R^1$ and $R^2$ are the same; each of m and n is 0; $Y^5$ is hydrogen; each $Y^{3a}$ and $Y^{3b}$ is deuterium; and the compound is selected from any one of the compounds set forth in Table 3b (below):

TABLE 3b

Exemplary Embodiments of Formula Ib

| Compound # | $R^1/R^2$ | $R^3$ | $R^4$ | $R^5$ | $Y^1$ |
|---|---|---|---|---|---|
| 200b | $CD_3$ | $CD_2$ | $CD_2$ | $CH_2$ | H |
| 201b | $CD_3$ | $CD_2$ | $CD_2$ | $CD_2$ | H |
| 202b | $CD_3$ | $CD_2$ | $CH_2$ | $CH_2$ | H |
| 203b | $CD_3$ | $CD_2$ | $CH_2$ | $CD_2$ | H |
| 204b | $CD_3$ | $CD_2$ | $CD_2$ | $CH_2$ | D |
| 205b | $CD_3$ | $CD_2$ | $CD_2$ | $CD_2$ | D |
| 206b | $CD_3$ | $CD_2$ | $CH_2$ | $CH_2$ | D |
| 207b | $CD_3$ | $CD_2$ | $CH_2$ | $CD_2$ | D |
| 208b | $CH_3$ | $CH_2$ | $CD_2$ | $CH_2$ | H |
| 209b | $CH_3$ | $CH_2$ | $CD_2$ | $CD_2$ | H |
| 210b | $CH_3$ | $CH_2$ | $CH_2$ | $CD_2$ | H |
| 211b | $CH_3$ | $CH_2$ | $CD_2$ | $CH_2$ | D |
| 212b | $CH_3$ | $CH_2$ | $CD_2$ | $CD_2$ | D |
| 213b | $CH_3$ | $CH_2$ | $CH_2$ | $CH_2$ | D |
| 214b | $CH_3$ | $CH_2$ | $CH_2$ | $CD_2$ | D |
| 215b | $CD_3$ | $CH_2$ | $CH_2$ | $CH_2$ | H |
| 216b | $CD_3$ | $CH_2$ | $CD_2$ | $CH_2$ | H |
| 217b | $CD_3$ | $CH_2$ | $CD_2$ | $CD_2$ | H |
| 218b | $CD_3$ | $CH_2$ | $CH_2$ | $CD_2$ | H |
| 219b | $CD_3$ | $CH_2$ | $CD_2$ | $CH_2$ | D |
| 220b | $CD_3$ | $CH_2$ | $CD_2$ | $CD_2$ | D |
| 221b | $CD_3$ | $CH_2$ | $CH_2$ | $CH_2$ | D |
| 222b | $CD_3$ | $CH_2$ | $CH_2$ | $CD_2$ | D |
| 223b | $CH_3$ | $CD_2$ | $CD_2$ | $CH_2$ | H |
| 224b | $CH_3$ | $CD_2$ | $CD_2$ | $CD_2$ | H |
| 225b | $CH_3$ | $CD_2$ | $CH_2$ | $CD_2$ | H |
| 226b | $CH_3$ | $CD_2$ | $CH_2$ | $CH_2$ | H |
| 227b | $CH_3$ | $CD_2$ | $CD_2$ | $CH_2$ | D |
| 228b | $CH_3$ | $CD_2$ | $CD_2$ | $CD_2$ | D |
| 229b | $CH_3$ | $CD_2$ | $CH_2$ | $CH_2$ | D |
| 230b | $CH_3$ | $CD_2$ | $CH_2$ | $CD_2$ | D |
| 231b | $CH_3$ | $CH_2$ | $CH_2$ | $CH_2$ | H | or a pharmaceutically acceptable salt thereof.

In one embodiment of a compound of Formula II, $R^1$ and $R^2$ are the same; each of m and n is 0; $Y^5$ is hydrogen; each $Y^{3a}$ and $Y^{3b}$ is hydrogen; and the compound is selected from any one of the compounds set forth in Table 1a (below):

TABLE 4a

Exemplary Embodiments of Formula II

| Compound # | $R^1/R^2$ | $R^3$ | $R^4$ | $R^5$ | $Y^1$ |
|---|---|---|---|---|---|
| 300 | $CD_3$ | $CD_2$ | $CD_2$ | $CH_2$ | H |
| 301 | $CD_3$ | $CD_2$ | $CD_2$ | $CD_2$ | H |
| 302 | $CD_3$ | $CD_2$ | $CH_2$ | $CH_2$ | H |
| 303 | $CD_3$ | $CD_2$ | $CH_2$ | $CD_2$ | H |
| 304 | $CD_3$ | $CD_2$ | $CD_2$ | $CH_2$ | D |
| 305 | $CD_3$ | $CD_2$ | $CD_2$ | $CD_2$ | D |
| 306 | $CD_3$ | $CD_2$ | $CH_2$ | $CH_2$ | D |
| 307 | $CD_3$ | $CD_2$ | $CH_2$ | $CD_2$ | D |
| 308 | $CH_3$ | $CH_2$ | $CD_2$ | $CH_2$ | H |
| 309 | $CH_3$ | $CH_2$ | $CD_2$ | $CD_2$ | H |
| 310 | $CH_3$ | $CH_2$ | $CH_2$ | $CD_2$ | H |
| 311 | $CH_3$ | $CH_2$ | $CD_2$ | $CH_2$ | D |
| 312 | $CH_3$ | $CH_2$ | $CD_2$ | $CD_2$ | D |
| 313 | $CH_3$ | $CH_2$ | $CH_2$ | $CH_2$ | D |
| 314 | $CH_3$ | $CH_2$ | $CH_2$ | $CD_2$ | D |
| 315 | $CD_3$ | $CH_2$ | $CH_2$ | $CH_2$ | H |
| 316 | $CD_3$ | $CH_2$ | $CD_2$ | $CH_2$ | H |
| 317 | $CD_3$ | $CH_2$ | $CD_2$ | $CD_2$ | H |
| 318 | $CD_3$ | $CH_2$ | $CH_2$ | $CD_2$ | H |
| 319 | $CD_3$ | $CH_2$ | $CD_2$ | $CH_2$ | D |
| 320 | $CD_3$ | $CH_2$ | $CD_2$ | $CD_2$ | D |
| 321 | $CD_3$ | $CH_2$ | $CH_2$ | $CH_2$ | D |
| 322 | $CD_3$ | $CH_2$ | $CH_2$ | $CD_2$ | D |
| 323 | $CH_3$ | $CD_2$ | $CD_2$ | $CH_2$ | H |
| 324 | $CH_3$ | $CD_2$ | $CD_2$ | $CD_2$ | H |
| 325 | $CH_3$ | $CD_2$ | $CH_2$ | $CD_2$ | H |
| 326 | $CH_3$ | $CD_2$ | $CH_2$ | $CH_2$ | H |
| 327 | $CH_3$ | $CD_2$ | $CD_2$ | $CH_2$ | D |
| 328 | $CH_3$ | $CD_2$ | $CD_2$ | $CD_2$ | D |
| 329 | $CH_3$ | $CD_2$ | $CH_2$ | $CH_2$ | D |
| 330 | $CH_3$ | $CD_2$ | $CH_2$ | $CD_2$ | D |
| 331 | $CH_3$ | $CH_2$ | $CH_2$ | $CH_2$ | H | or a pharmaceutically acceptable salt thereof.

In one embodiment of a compound of Formula II, $R^1$ and $R^2$ are the same; each of m and n is 0; $Y^5$ is hydrogen; each $Y^{3a}$ and $Y^{3b}$ is deuterium; and the compound is selected from any one of the compounds set forth in Table 4b (below):

TABLE 4b

Exemplary Embodiments of Formula II

| Compound # | $R^1/R^2$ | $R^3$ | $R^4$ | $R^5$ | $Y^1$ |
|---|---|---|---|---|---|
| 400 | $CD_3$ | $CD_2$ | $CD_2$ | $CH_2$ | H |
| 401 | $CD_3$ | $CD_2$ | $CD_2$ | $CD_2$ | H |
| 402 | $CD_3$ | $CD_2$ | $CH_2$ | $CH_2$ | H |
| 403 | $CD_3$ | $CD_2$ | $CH_2$ | $CD_2$ | H |
| 404 | $CD_3$ | $CD_2$ | $CD_2$ | $CH_2$ | D |
| 405 | $CD_3$ | $CD_2$ | $CD_2$ | $CD_2$ | D |
| 406 | $CD_3$ | $CD_2$ | $CH_2$ | $CH_2$ | D |
| 407 | $CD_3$ | $CD_2$ | $CH_2$ | $CD_2$ | D |
| 408 | $CH_3$ | $CH_2$ | $CH_2$ | $CH_2$ | H |
| 409 | $CH_3$ | $CH_2$ | $CD_2$ | $CD_2$ | H |
| 410 | $CH_3$ | $CH_2$ | $CD_2$ | $CD_2$ | H |
| 411 | $CH_3$ | $CH_2$ | $CH_2$ | $CD_2$ | D |
| 412 | $CH_3$ | $CH_2$ | $CD_2$ | $CD_2$ | D |
| 413 | $CH_3$ | $CH_2$ | $CH_2$ | $CH_2$ | D |
| 414 | $CH_3$ | $CH_2$ | $CH_2$ | $CD_2$ | D |
| 415 | $CD_3$ | $CH_2$ | $CH_2$ | $CH_2$ | H |
| 416 | $CD_3$ | $CH_2$ | $CD_2$ | $CH_2$ | H |
| 417 | $CD_3$ | $CH_2$ | $CD_2$ | $CD_2$ | H |
| 418 | $CD_3$ | $CH_2$ | $CH_2$ | $CD_2$ | H |
| 419 | $CD_3$ | $CH_2$ | $CD_2$ | $CH_2$ | D |
| 420 | $CD_3$ | $CH_2$ | $CD_2$ | $CD_2$ | D |
| 421 | $CD_3$ | $CH_2$ | $CH_2$ | $CH_2$ | D |
| 422 | $CD_3$ | $CH_2$ | $CH_2$ | $CD_2$ | D |
| 423 | $CH_3$ | $CD_2$ | $CD_2$ | $CH_2$ | H |

TABLE 4b-continued

Exemplary Embodiments of Formula II

| Compound # | $R^1/R^2$ | $R^3$ | $R^4$ | $R^5$ | $Y^1$ |
|---|---|---|---|---|---|
| 424 | $CH_3$ | $CD_2$ | $CD_2$ | $CD_2$ | H |
| 425 | $CH_3$ | $CD_2$ | $CH_2$ | $CD_2$ | H |
| 426 | $CH_3$ | $CD_2$ | $CH_2$ | $CH_2$ | H |
| 427 | $CH_3$ | $CD_2$ | $CD_2$ | $CH_2$ | D |
| 428 | $CH_3$ | $CD_2$ | $CD_2$ | $CD_2$ | D |
| 429 | $CH_3$ | $CD_2$ | $CH_2$ | $CH_2$ | D |
| 430 | $CH_3$ | $CD_2$ | $CH_2$ | $CD_2$ | D |
| 431 | $CH_3$ | $CH_2$ | $CH_2$ | $CH_2$ | H | or a pharmaceutically acceptable salt thereof.

In one embodiment of a compound of Formula IIa, $R^1$ and $R^2$ are the same; each of m and n is 0; $Y^5$ is hydrogen; each $Y^{3a}$ and $Y^{3b}$ is hydrogen; and the compound is selected from any one of the compounds set forth in Table 5a (below):

TABLE 5a

Exemplary Embodiments of Formula IIa

| Compound # | $R^1/R^2$ | $R^3$ | $R^4$ | $R^5$ | $Y^1$ |
|---|---|---|---|---|---|
| 300a | $CD_3$ | $CD_2$ | $CD_2$ | $CH_2$ | H |
| 301a | $CD_3$ | $CD_2$ | $CD_2$ | $CD_2$ | H |
| 302a | $CD_3$ | $CD_2$ | $CH_2$ | $CH_2$ | H |
| 303a | $CD_3$ | $CD_2$ | $CH_2$ | $CD_2$ | H |
| 304a | $CD_3$ | $CD_2$ | $CD_2$ | $CH_2$ | D |
| 305a | $CD_3$ | $CD_2$ | $CD_2$ | $CD_2$ | D |
| 306a | $CD_3$ | $CD_2$ | $CH_2$ | $CH_2$ | D |
| 307a | $CD_3$ | $CD_2$ | $CH_2$ | $CD_2$ | D |
| 308a | $CH_3$ | $CH_2$ | $CD_2$ | $CH_2$ | H |
| 309a | $CH_3$ | $CH_2$ | $CD_2$ | $CD_2$ | H |
| 310a | $CH_3$ | $CH_2$ | $CH_2$ | $CD_2$ | H |
| 311a | $CH_3$ | $CH_2$ | $CD_2$ | $CH_2$ | D |
| 312a | $CH_3$ | $CH_2$ | $CD_2$ | $CD_2$ | D |
| 313a | $CH_3$ | $CH_2$ | $CH_2$ | $CD_2$ | D |
| 314a | $CH_3$ | $CH_2$ | $CH_2$ | $CD_2$ | D |
| 315a | $CD_3$ | $CH_2$ | $CD_2$ | $CH_2$ | H |
| 316a | $CD_3$ | $CH_2$ | $CD_2$ | $CD_2$ | H |
| 317a | $CD_3$ | $CH_2$ | $CH_2$ | $CH_2$ | H |
| 318a | $CD_3$ | $CH_2$ | $CH_2$ | $CD_2$ | H |
| 319a | $CD_3$ | $CH_2$ | $CD_2$ | $CH_2$ | D |
| 320a | $CD_3$ | $CH_2$ | $CD_2$ | $CD_2$ | D |
| 321a | $CD_3$ | $CH_2$ | $CH_2$ | $CH_2$ | D |
| 322a | $CD_3$ | $CH_2$ | $CH_2$ | $CD_2$ | D |
| 323a | $CH_3$ | $CD_2$ | $CD_2$ | $CH_2$ | H |
| 324a | $CH_3$ | $CD_2$ | $CD_2$ | $CD_2$ | H |
| 325a | $CH_3$ | $CD_2$ | $CH_2$ | $CH_2$ | H |
| 326a | $CH_3$ | $CD_2$ | $CH_2$ | $CH_2$ | H |
| 327a | $CH_3$ | $CD_2$ | $CD_2$ | $CH_2$ | D |
| 328a | $CH_3$ | $CD_2$ | $CD_2$ | $CD_2$ | D |
| 329a | $CH_3$ | $CD_2$ | $CH_2$ | $CH_2$ | D |
| 330a | $CH_3$ | $CD_2$ | $CH_2$ | $CD_2$ | D |
| 331a | $CH_3$ | $CH_2$ | $CH_2$ | $CH_2$ | H | or a pharmaceutically acceptable salt thereof.

In one embodiment of a compound of Formula IIa, $R^1$ and $R^2$ are the same; each of m and n is 0; $Y^5$ is hydrogen; each $Y^{3a}$ and $Y^{3b}$ is deuterium; and the compound is selected from any one of the compounds set forth in Table 5b (below):

TABLE 5b

Exemplary Embodiments of Formula IIa

| Compound # | $R^1/R^2$ | $R^3$ | $R^4$ | $R^5$ | $Y^1$ |
|---|---|---|---|---|---|
| 400a | $CD_3$ | $CD_2$ | $CD_2$ | $CH_2$ | H |
| 401a | $CD_3$ | $CD_2$ | $CD_2$ | $CD_2$ | H |
| 402a | $CD_3$ | $CD_2$ | $CH_2$ | $CH_2$ | H |
| 403a | $CD_3$ | $CD_2$ | $CH_2$ | $CD_2$ | H |

TABLE 5b-continued

Exemplary Embodiments of Formula IIa

| Compound # | $R^1/R^2$ | $R^3$ | $R^4$ | $R^5$ | $Y^1$ |
|---|---|---|---|---|---|
| 404a | $CD_3$ | $CD_2$ | $CD_2$ | $CH_2$ | D |
| 405a | $CD_3$ | $CD_2$ | $CD_2$ | $CD_2$ | D |
| 406a | $CD_3$ | $CD_2$ | $CH_2$ | $CH_2$ | D |
| 407a | $CD_3$ | $CD_2$ | $CH_2$ | $CD_2$ | D |
| 408a | $CH_3$ | $CH_2$ | $CD_2$ | $CH_2$ | H |
| 409a | $CH_3$ | $CH_2$ | $CD_2$ | $CD_2$ | H |
| 410a | $CH_3$ | $CH_2$ | $CH_2$ | $CD_2$ | H |
| 411a | $CH_3$ | $CH_2$ | $CD_2$ | $CH_2$ | D |
| 412a | $CH_3$ | $CH_2$ | $CD_2$ | $CD_2$ | D |
| 413a | $CH_3$ | $CH_2$ | $CH_2$ | $CH_2$ | D |
| 414a | $CH_3$ | $CH_2$ | $CH_2$ | $CD_2$ | D |
| 415a | $CD_3$ | $CH_2$ | $CD_2$ | $CH_2$ | H |
| 416a | $CD_3$ | $CH_2$ | $CD_2$ | $CD_2$ | H |
| 417a | $CD_3$ | $CH_2$ | $CH_2$ | $CH_2$ | H |
| 418a | $CD_3$ | $CH_2$ | $CH_2$ | $CD_2$ | H |
| 419a | $CD_3$ | $CH_2$ | $CD_2$ | $CH_2$ | D |
| 420a | $CD_3$ | $CH_2$ | $CD_2$ | $CD_2$ | D |
| 421a | $CD_3$ | $CH_2$ | $CH_2$ | $CH_2$ | D |
| 422a | $CD_3$ | $CH_2$ | $CH_2$ | $CD_2$ | D |
| 423a | $CH_3$ | $CD_2$ | $CD_2$ | $CH_2$ | H |
| 424a | $CH_3$ | $CD_2$ | $CD_2$ | $CD_2$ | H |
| 425a | $CH_3$ | $CD_2$ | $CH_2$ | $CD_2$ | H |
| 426a | $CH_3$ | $CD_2$ | $CH_2$ | $CH_2$ | H |
| 427a | $CH_3$ | $CD_2$ | $CD_2$ | $CH_2$ | D |
| 428a | $CH_3$ | $CD_2$ | $CD_2$ | $CD_2$ | D |
| 429a | $CH_3$ | $CD_2$ | $CH_2$ | $CH_2$ | D |
| 430a | $CH_3$ | $CD_2$ | $CH_2$ | $CD_2$ | D |
| 431a | $CH_3$ | $CH_2$ | $CH_2$ | $CH_2$ | H | or a pharmaceutically acceptable salt thereof.

In one embodiment of a compound of Formula IIb, $R^1$ and $R^2$ are the same; each of m and n is 0; $Y^5$ is hydrogen; each $Y^{3a}$ and $Y^{3b}$ is hydrogen; and the compound is selected from any one of the compounds set forth in Table 6a (below):

TABLE 6a

Exemplary Embodiments of Formula IIb

| Compound # | $R^1/R^2$ | $R^3$ | $R^4$ | $R^5$ | $Y^1$ |
|---|---|---|---|---|---|
| 300b | $CD_3$ | $CD_2$ | $CD_2$ | $CH_2$ | H |
| 301b | $CD_3$ | $CD_2$ | $CD_2$ | $CD_2$ | H |
| 302b | $CD_3$ | $CD_2$ | $CH_2$ | $CH_2$ | H |
| 303b | $CD_3$ | $CD_2$ | $CH_2$ | $CD_2$ | H |
| 304b | $CD_3$ | $CD_2$ | $CD_2$ | $CH_2$ | D |
| 305b | $CD_3$ | $CD_2$ | $CD_2$ | $CD_2$ | D |
| 306b | $CD_3$ | $CD_2$ | $CH_2$ | $CH_2$ | D |
| 307b | $CD_3$ | $CD_2$ | $CH_2$ | $CD_2$ | D |
| 308b | $CH_3$ | $CH_2$ | $CD_2$ | $CH_2$ | H |
| 309b | $CH_3$ | $CH_2$ | $CD_2$ | $CD_2$ | H |
| 310b | $CH_3$ | $CH_2$ | $CH_2$ | $CD_2$ | H |
| 311b | $CH_3$ | $CH_2$ | $CD_2$ | $CH_2$ | D |
| 312b | $CH_3$ | $CH_2$ | $CD_2$ | $CD_2$ | D |
| 313b | $CH_3$ | $CH_2$ | $CH_2$ | $CH_2$ | D |
| 314b | $CH_3$ | $CH_2$ | $CH_2$ | $CD_2$ | D |
| 315b | $CD_3$ | $CH_2$ | $CD_2$ | $CH_2$ | H |
| 316b | $CD_3$ | $CH_2$ | $CD_2$ | $CD_2$ | H |
| 317b | $CD_3$ | $CH_2$ | $CH_2$ | $CH_2$ | H |
| 318b | $CD_3$ | $CH_2$ | $CH_2$ | $CD_2$ | H |
| 319b | $CD_3$ | $CH_2$ | $CD_2$ | $CH_2$ | D |
| 320b | $CD_3$ | $CH_2$ | $CD_2$ | $CD_2$ | D |
| 321b | $CD_3$ | $CH_2$ | $CH_2$ | $CH_2$ | D |
| 322b | $CD_3$ | $CH_2$ | $CH_2$ | $CD_2$ | D |
| 323b | $CH_3$ | $CD_2$ | $CD_2$ | $CH_2$ | H |
| 324b | $CH_3$ | $CD_2$ | $CD_2$ | $CD_2$ | H |
| 325b | $CH_3$ | $CD_2$ | $CH_2$ | $CH_2$ | H |
| 326b | $CH_3$ | $CD_2$ | $CH_2$ | $CH_2$ | H |
| 327b | $CH_3$ | $CD_2$ | $CD_2$ | $CH_2$ | D |
| 328b | $CH_3$ | $CD_2$ | $CD_2$ | $CD_2$ | D |

TABLE 6a-continued

Exemplary Embodiments of Formula IIb

| Compound # | R¹/R² | R³ | R⁴ | R⁵ | Y¹ |
|---|---|---|---|---|---|
| 329b | CH₃ | CD₂ | CH₂ | CH₂ | D |
| 330b | CH₃ | CD₂ | CH₂ | CD₂ | D |
| 331b | CH₃ | CH₂ | CH₂ | CH₂ | H | or a pharmaceutically acceptable salt thereof.

In one embodiment of a compound of Formula IIb, $R^1$ and $R^2$ are the same; each of m and n is 0; $Y^5$ is hydrogen; each $Y^{3a}$ and $Y^{3b}$ is deuterium; and the compound is selected from any one of the compounds set forth in Table 6b (below):

TABLE 6b

Exemplary Embodiments of Formula IIb

| Compound # | R¹/R² | R³ | R⁴ | R⁵ | Y¹ |
|---|---|---|---|---|---|
| 400b | CD₃ | CD₂ | CD₂ | CH₂ | H |
| 401b | CD₃ | CD₂ | CD₂ | CD₂ | H |
| 402b | CD₃ | CD₂ | CH₂ | CH₂ | H |
| 403b | CD₃ | CD₂ | CH₂ | CD₂ | H |
| 404b | CD₃ | CD₂ | CD₂ | CH₂ | D |
| 405b | CD₃ | CD₂ | CD₂ | CD₂ | D |
| 406b | CD₃ | CD₂ | CH₂ | CH₂ | D |
| 407b | CD₃ | CD₂ | CH₂ | CD₂ | D |
| 408b | CH₃ | CH₂ | CD₂ | CH₂ | H |
| 409b | CH₃ | CH₂ | CD₂ | CD₂ | H |
| 410b | CH₃ | CH₂ | CH₂ | CD₂ | H |
| 411b | CH₃ | CH₂ | CD₂ | CH₂ | D |
| 412b | CH₃ | CH₂ | CD₂ | CD₂ | D |
| 413b | CH₃ | CH₂ | CH₂ | CH₂ | D |
| 414b | CH₃ | CH₂ | CH₂ | CD₂ | D |
| 415b | CD₃ | CH₂ | CD₂ | CH₂ | H |
| 416b | CD₃ | CH₂ | CD₂ | CD₂ | H |
| 417b | CD₃ | CH₂ | CH₂ | CH₂ | H |
| 418b | CD₃ | CH₂ | CH₂ | CD₂ | H |
| 419b | CD₃ | CH₂ | CD₂ | CH₂ | D |
| 420b | CD₃ | CH₂ | CD₂ | CD₂ | D |
| 421b | CD₃ | CH₂ | CH₂ | CH₂ | D |
| 422b | CD₃ | CH₂ | CH₂ | CD₂ | D |
| 423b | CH₃ | CD₂ | CD₂ | CH₂ | H |
| 424b | CH₃ | CD₂ | CD₂ | CD₂ | H |
| 425b | CH₃ | CD₂ | CH₂ | CH₂ | H |
| 426b | CH₃ | CD₂ | CH₂ | CH₂ | H |
| 427b | CH₃ | CD₂ | CD₂ | CH₂ | D |
| 428b | CH₃ | CD₂ | CD₂ | CD₂ | D |
| 429b | CH₃ | CD₂ | CH₂ | CD₂ | D |
| 430b | CH₃ | CD₂ | CH₂ | CD₂ | D |
| 431b | CH₃ | CH₂ | CH₂ | CH₂ | H | or a pharmaceutically acceptable salt thereof.

In some embodiments, the compound is selected from:

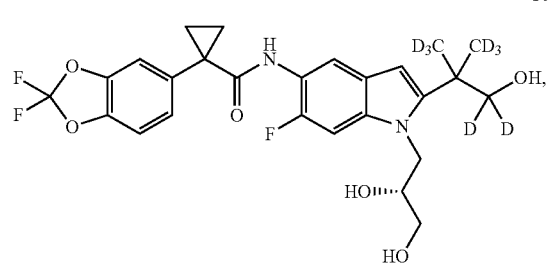

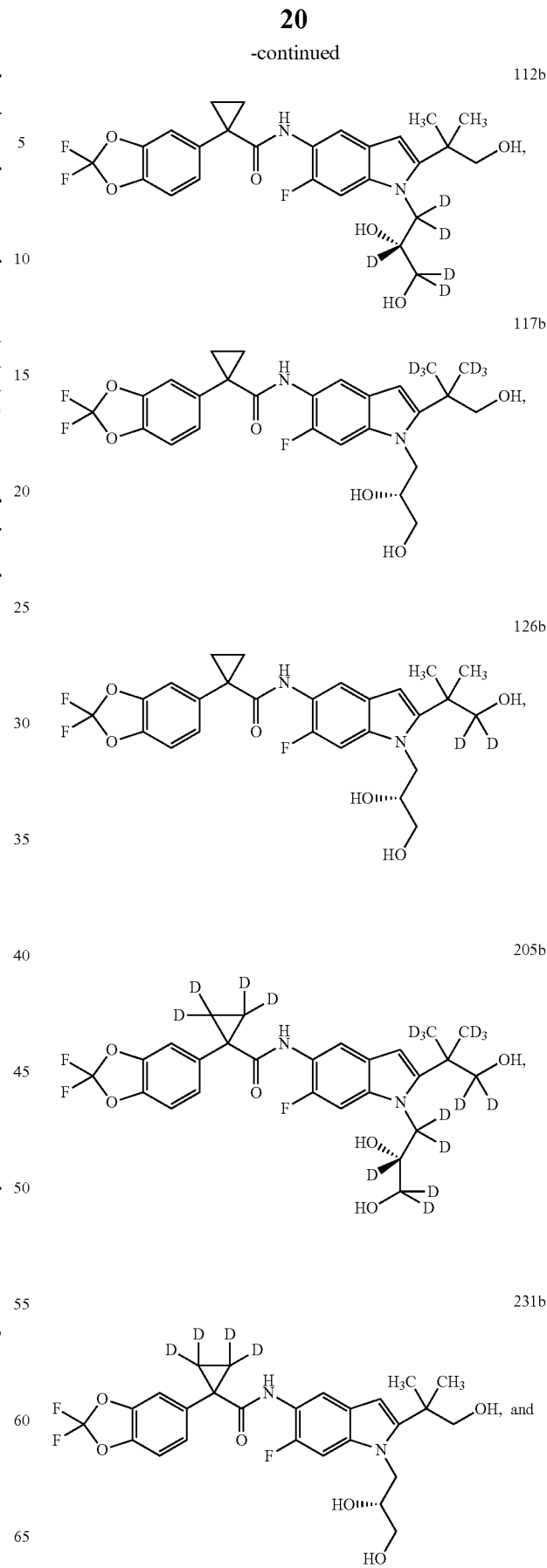

-continued

331b or a pharmaceutically acceptable salt wherein any atom not designated as deuterium is present at its natural isotopic abundance.

In some embodiments of a compound of this invention, the level of deuterium incorporation at each atom designated as deuterium in $R^1$ is at least 52.5%. In one aspect, the level of deuterium incorporation is at least 75%. In one aspect, the level of deuterium incorporation is at least 82.5%. In one aspect, the level of deuterium incorporation is at least 90%. In one aspect, the level of deuterium incorporation is at least 95%. In one aspect the level of deuterium incorporation is at least 97%. In one aspect the level of deuterium incorporation is at least 99%.

In some embodiments of a compound of this invention, the level of deuterium incorporation at each atom designated as deuterium in $R^2$ is at least 52.5%. In one aspect, the level of deuterium incorporation is at least 75%. In one aspect, the level of deuterium incorporation is at least 82.5%. In one aspect, the level of deuterium incorporation is at least 90%. In one aspect, the level of deuterium incorporation is at least 95%. In one aspect the level of deuterium incorporation is at least 97%. In one aspect the level of deuterium incorporation is at least 99%.

In some embodiments of a compound of this invention, the level of deuterium incorporation at each atom designated as deuterium in $R^3$ is at least 52.5%. In one aspect, the level of deuterium incorporation is at least 75%. In one aspect, the level of deuterium incorporation is at least 82.5%. In one aspect, the level of deuterium incorporation is at least 90%. In one aspect, the level of deuterium incorporation is at least 95%. In one aspect the level of deuterium incorporation is at least 97%. In one aspect the level of deuterium incorporation is at least 99%.

In some embodiments of a compound of this invention, the level of deuterium incorporation at each atom designated as deuterium in $R^4$ is at least 52.5%. In one aspect, the level of deuterium incorporation is at least 75%. In one aspect, the level of deuterium incorporation is at least 82.5%. In one aspect, the level of deuterium incorporation is at least 90%. In one aspect, the level of deuterium incorporation is at least 95%. In one aspect the level of deuterium incorporation is at least 97%. In one aspect the level of deuterium incorporation is at least 99%.

In some embodiments of a compound of this invention, the level of deuterium incorporation at each atom designated as deuterium in $R^5$ is at least 52.5%. In one aspect, the level of deuterium incorporation is at least 75%. In one aspect, the level of deuterium incorporation is at least 82.5%. In one aspect, the level of deuterium incorporation is at least 90%. In one aspect, the level of deuterium incorporation is at least 95%. In one aspect the level of deuterium incorporation is at least 97%. In one aspect the level of deuterium incorporation is at least 99%.

In some embodiments of a compound of this invention, when $Y^1$ is deuterium, the level of deuterium incorporation at $Y^1$ is at least 52.5%. In one aspect, the level of deuterium incorporation is at least 75%. In one aspect, the level of deuterium incorporation is at least 82.5%. In one aspect, the level of deuterium incorporation is at least 90%. In one aspect, the level of deuterium incorporation is at least 95%. In one aspect the level of deuterium incorporation is at least 97%. In one aspect the level of deuterium incorporation is at least 99%.

In some embodiments of a compound of this invention, the level of deuterium incorporation at each $Y^2$ is at least 52.5%. In one aspect, the level of deuterium incorporation is at least 75%. In one aspect, the level of deuterium incorporation is at least 82.5%. In one aspect, the level of deuterium incorporation is at least 90%. In one aspect, the level of deuterium incorporation is at least 95%. In one aspect the level of deuterium incorporation is at least 97%. In one aspect the level of deuterium incorporation is at least 99%.

In some embodiments of a compound of this invention, the level of deuterium incorporation at each $Y^{3a}$ is at 52.5%. In one aspect, the level of deuterium incorporation is at least 75%. In one aspect, the level of deuterium incorporation is at least 82.5%. In one aspect, the level of deuterium incorporation is at least 90%. In one aspect, the level of deuterium incorporation is at least 95%. In one aspect the level of deuterium incorporation is at least 97%. In one aspect the level of deuterium incorporation is at least 99%.

In some embodiments of a compound of this invention, the level of deuterium incorporation at each $Y^{3b}$ is at least 52.5%. In one aspect, the level of deuterium incorporation is at least 75%. In one aspect, the level of deuterium incorporation is at least 82.5%. In one aspect, the level of deuterium incorporation is at least 90%. In one aspect, the level of deuterium incorporation is at least 95%. In one aspect the level of deuterium incorporation is at least 97%. In one aspect the level of deuterium incorporation is at least 99%.

In some embodiments of a compound of this invention, the level of deuterium incorporation at each $Y^4$ is at least 52.5%. In one aspect, the level of deuterium incorporation is at least 75%. In one aspect, the level of deuterium incorporation is at least 82.5%. In one aspect, the level of deuterium incorporation is at least 90%. In one aspect, the level of deuterium incorporation is at least 95%. In one aspect the level of deuterium incorporation is at least 97%. In one aspect the level of deuterium incorporation is at least 99%.

In some embodiments of a compound of this invention, when $Y^5$ is deuterium, the level of deuterium incorporation at $Y^5$ is at least 52.5%. In one aspect, the level of deuterium incorporation is at least 75%. In one aspect, the level of deuterium incorporation is at least 82.5%. In one aspect, the level of deuterium incorporation is at least 90%. In one aspect, the level of deuterium incorporation is at least 95%. In one aspect the level of deuterium incorporation is at least 97%. In one aspect the level of deuterium incorporation is at least 99%.

The present invention also provides deuterated intermediates useful, e.g., in the preparation of the compounds of Formula A, I, Ia, Ib, II, IIa and IIb. In certain embodiments, the intermediate is a compound of Formula III:

(III)

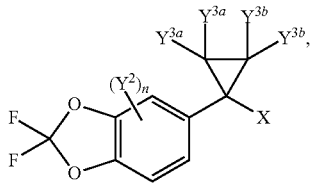

or a salt thereof, wherein each $Y^{3a}$ and each $Y^{3b}$ is selected from hydrogen and deuterium; each $Y^2$, if present, is deuterium; n is 0, 1, 2, or 3; and X is —CN, —CO$_2$H or —COCl, wherein at least one of $Y^{3a}$ and $Y^{3b}$ is deuterium or n is not 0. In one aspect of these embodiments, each $Y^{3a}$ and each $Y^{3b}$ is hydrogen. In another aspect of these embodiments, each $Y^{3a}$ and each $Y^{3b}$ is deuterium. In a further aspect, n is 0. In an alternative further aspect, n is 3.

In certain embodiments, the intermediate is a compound of Formula IV:

(IV)

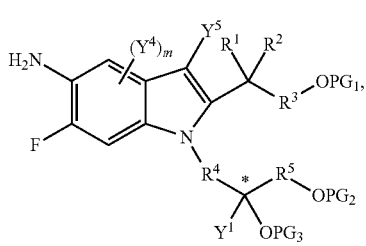

or a salt thereof, wherein each of $R^1$ and $R^2$ is independently selected from —CH$_3$, —CH$_2$D, —CHD$_2$, and —CD$_3$; each of $R^3$, $R^4$ and $R^5$ is independently selected from —CH$_2$—, —CHD- and —CD$_2$-; $Y^1$ is selected from hydrogen and deuterium; $Y^5$ is selected from hydrogen and deuterium; each $Y^4$, if present, is deuterium;
m is 0, 1, or 2; each PG is independently selected from hydrogen and an alcohol protecting group, wherein at least one of $Y^1$, $Y^5$, $R^1$, $R^2$, $R^3$, $R^4$ and $R^5$, comprises deuterium or m is not 0.

In one embodiment of a compound of Formula IV, each of $R^1$ and $R^2$ is —CD$_3$. In another embodiment, each of $R^1$ and $R^2$ is —CH$_3$. In one aspect of these embodiments, at least one of $R^3$, $R^4$, and $R^5$ is —CD$_2$-. In one example of this aspect $R^3$ is —CD$_2$-. In another example of this aspect $R^4$ is —CD$_2$-. In another example of this aspect $R^5$ is —CD$_2$-. In one aspect of these embodiments, $Y^1$ is deuterium. In one aspect of these embodiments, $Y^5$ is deuterium and m is 2. In an alternate aspect of these embodiments, $Y^5$ is hydrogen and m is 0. In one aspect of these embodiments, at least one of PG1, PG2 and PG3 is an alcohol protecting group selected from acetoxy (Ac), benzyl (Bn), benzoyl (Bz), methoxyethoxymethyl ether (MEM), dimethoxytrityl (DMT), methoxymethyl ether (MOM), methoxytrityl (MMT), p-methoxybenzyl ether (PMB), methylthiomethyl ether, pivaloyl (Piv), tetrahydropyranyl (THP), tetrahydrofuryl (THF), trityl (Tr), silyl ether (for example—TMS, TBDMS, TOM, TIPS), methyl and ethoxyethyl (EE). These protecting groups and further examples of alcohol protecting groups can be found in Greene, T W et al., *Protective Groups in Organic Synthesis,* 4th Ed., John Wiley and Sons (2007). In a more specific aspect of these embodiments, at least one of PG1, PG2 and PG3 is Bn.

In certain embodiments, the intermediate is a compound of Formula V:

(V)

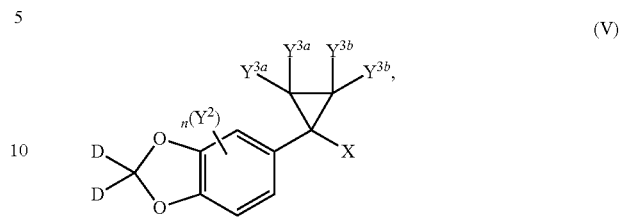

or a salt thereof, wherein each $Y^{3a}$ and each $Y^{3b}$ is selected from hydrogen and deuterium; each $Y^2$, if present, is deuterium; n is 0, 1, 2, or 3; and X is —CN, —CO$_2$H or —COCl, wherein at least one of $Y^{3a}$ and $Y^{3b}$ is deuterium or n is not 0. In one aspect of these embodiments, each $Y^{3a}$ and each $Y^{3b}$ is hydrogen. In another aspect of these embodiments, each $Y^{3a}$ and each $Y^{3b}$ is deuterium. In a further aspect, n is 0. In an alternative further aspect, n is 3.

In another set of embodiments, any atom not designated as deuterium in any of the embodiments set forth above is present at its natural isotopic abundance.

The synthesis of compounds of Formula A, I, Ia, Ib, II, IIa and IIb may be readily achieved by synthetic chemists of ordinary skill by reference to the Exemplary Synthesis and Examples disclosed herein. Relevant procedures analogous to those of use for the preparation of compounds of Formula A, I, Ia, Ib, II, IIa and IIb and intermediates thereof are disclosed, for instance in WO2010053471 and WO2011133751.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

A convenient method for synthesizing compounds of Formula I, Ia and Ib is depicted in the schemes set forth below.

Scheme 1: General Synthesis of Compounds of Formula I, Ia, and Ib

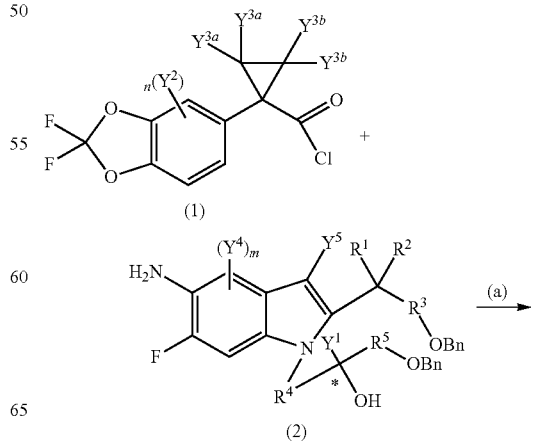

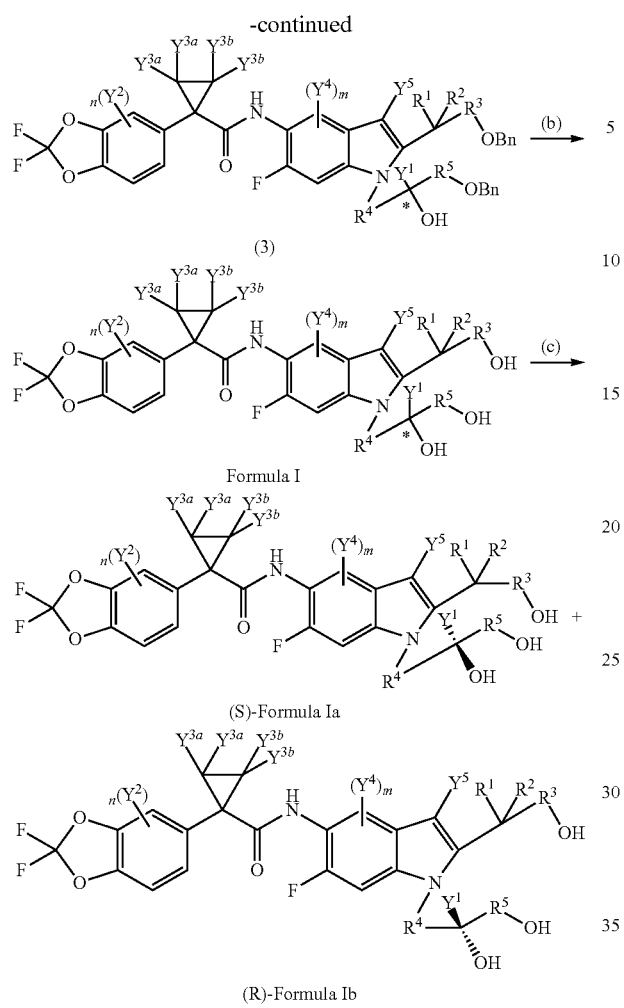

Formula I (S)-Formula Ia (R)-Formula Ib

Reagents and conditions: (a) Et₃N; (b) H₂, Pd/C, HCl—MeOH; (c) Chiral Separation In a manner analogous to a procedure described in WO2010053471 and US2013116238, appropriately deuterated acid chloride intermediate (1) is treated with appropriately deuterated and protected amino indole intermediate (2) to produce corresponding deuterated and protected hydroxyamide intermediate (3). Subsequent removal of protecting group of the hydroxyl moiety by hydrogenolysis using Pd—C furnishes appropriately deuterated compounds of Formula I which is separated by chiral chromatography to produce compounds of Formula Ia and Formula Ib.

It will be appreciated by anyone skilled in the art that compounds of Formula I contain an asymmetric center and a suitable procedure for preparation of a racemic mixture of said compounds is shown in Scheme 1. In this instance, a conventional method such as chiral chromatography is used to resolve appropriately deuterated racemic compounds of Formula I to produce enantiomers Formula Ia and Formula Ib. Compounds of Formula Ia and Formula Ib may also be produced using chiral forms of epoxide intermediate (12) (vide infra) by procedures disclosed as referenced above, also for instance in WO 2011133751 thereby directly producing enantiomers, Formula Ia and Formula Ib. When appropriately deuterated enantiomeric form of intermediate (2) is employed, chiral separation step is omitted in compound production.

Using commercially available reagents and deuterated reagents that can be readily prepared by known methods, compounds of Formula I, Ia, and Ib can be prepared with greater than 90% or greater than 95% deuterium incorporation at each position designated as D (see below for details).

Appropriately deuterated intermediate (1), for use in the preparation of compounds of Formula I, Ia, and Ib according to Scheme 1 may be prepared from corresponding deuterated reagents exemplified in Scheme 2.

Scheme 2: Preparation of Intermediate (1)

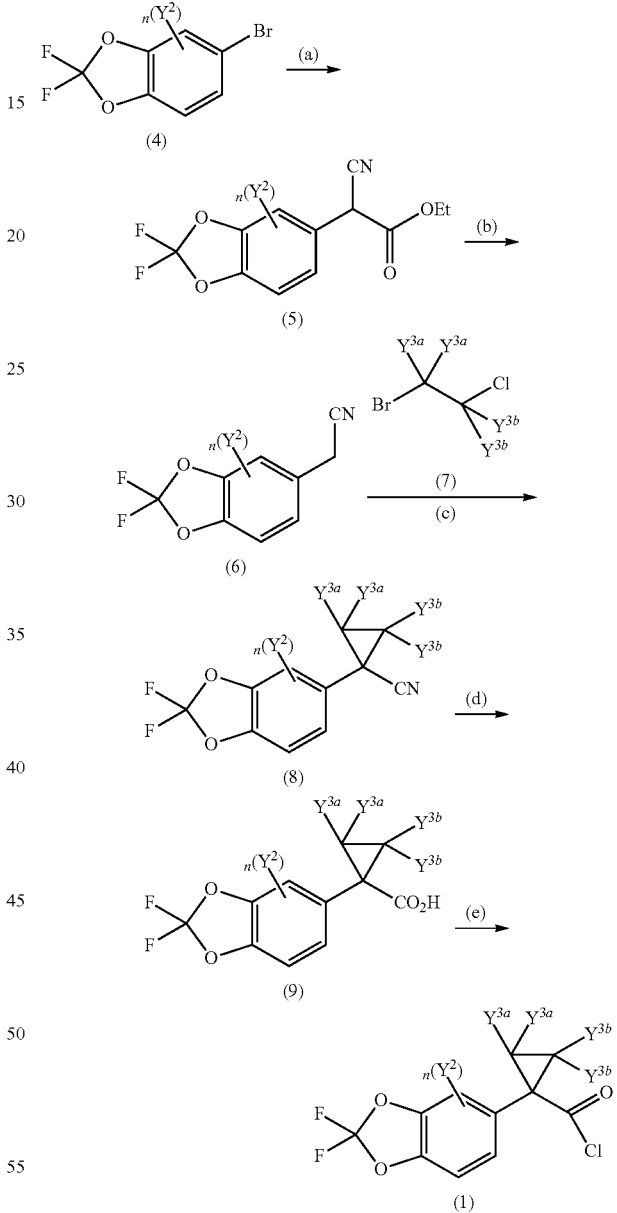

Reactions and conditions: (a) Ethyl cyanoacetate, Pd(dba)₂, t-Bu₃P, Na₃PO₄; (b) 3N HCl; (c) NaOH, Bu₄NBr; (d) NaOH, HCl; (e) SOCl₂

Appropriately deuterated cyanoester intermediate (5) is prepared from appropriately deuterated aryl halide (4) in a manner analogous to a procedure described in WO 2011133751 in the presence of transition metal catalyst. Decarboxylation of intermediate (5) with an acid such as HCl produces appropriately deuterated cyano methyl intermediate (6), which is subsequently treated with appropriately deuterated dihalide intermediate (7) in the presence of a base such as NaOH to provide appropriately deuterated cycloalkyl intermediate (8). Hydrolysis of the cyano moiety produces appropriately deuterated carboxylic acid intermediate (9), which is halogenated to furnish appropriately deuterated acid halide intermediate (1).

Appropriately deuterated intermediate (2), for use in the preparation of compounds of Formula I, Ia, and Ib according to Scheme 1 may be prepared from corresponding deuterated reagents exemplified in Scheme 3.

Scheme 3: Preparation of Intermediate (2)

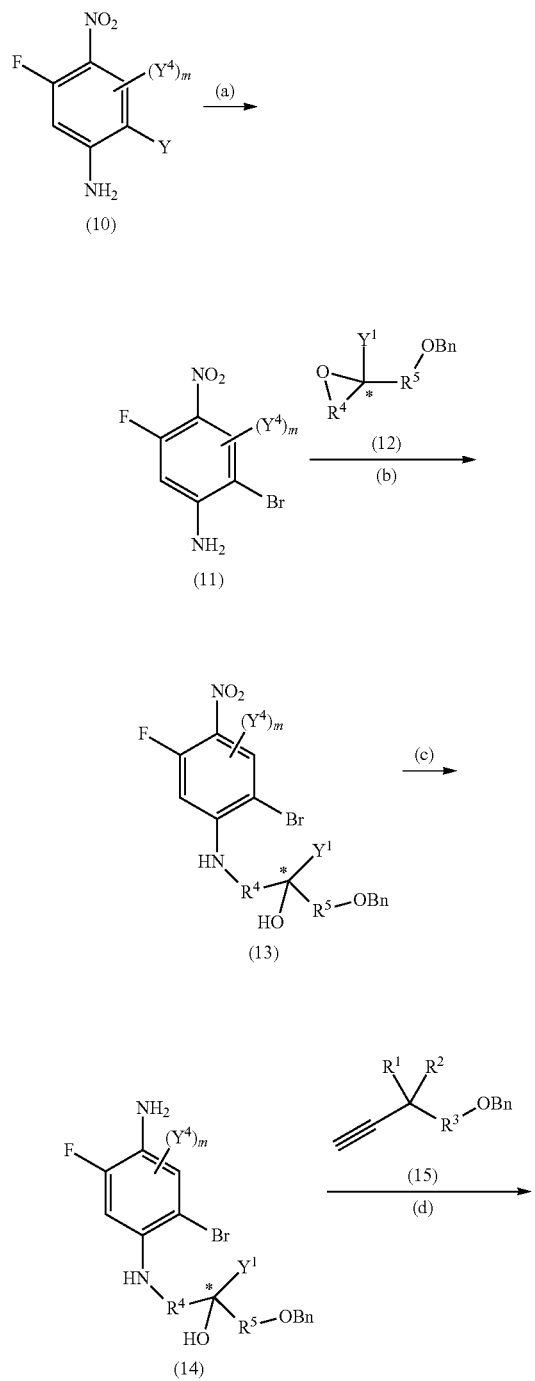

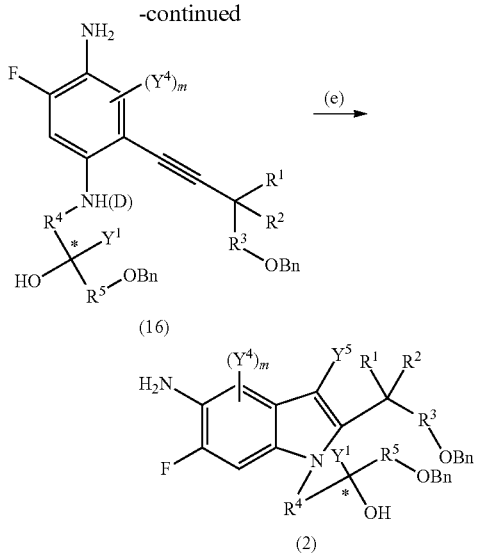

Reactions and conditions: (a) NBS; (b) Zn(ClO$_4$)$_2$·2H$_2$O; (c) H$_2$, Pt (S)/C; (d) Pd(OAc)$_2$, dppb, K$_2$CO$_3$, CuI, D$_2$O; (e) (MeCN)$_2$PdCl$_2$, CuI, CD$_3$CN Appropriately deuterated indole intermediate (2) is prepared in a manner analogous to the procedure described in WO 2011133751. Thus, appropriately deuterated nitro-aryl amine (10) is treated with a bromonium ion source such as NBS at room temperature to provide appropriately deuterated aryl bromide intermediate (11). Alkylation of (11) with appropriately deuterated and protected epoxide (12) in the presence of a Zn(II) catalyst such as zinc perchlorate dihydrate, effects a ring opening reaction to produce appropriately deuterated and protected amino alcohol intermediate (13). Hydrogenation of the nitro moiety of (13) using Pt affords appropriately deuterated aniline intermediate (14). Subsequent Sonogashira coupling reaction of appropriately deuterated benzyoxymethyl alkyne intermediate (15) in the presence of Pd(II) catalyst such as Pd(OAc)$_2$ replaces bromide moiety of intermediate (14) to furnish appropriately deuterated amino alkyne intermediate (16). Ring closure of intermediate (16) to produce appropriately deuterated and protected amino indole intermediate (2) is accomplished using another Pd(II) catalyst such as (MeCN)$_2$PdCl$_2$ in a suitable deuterated solvent such as CD$_3$CN. Use of appropriately deuterated reagents allows deuterium incorporation at the Y$^5$ position of a compound of Formula I, Ia, or Ib, or any appropriate intermediate herein, e.g., 90, 95, 97, or 99% deuterium incorporation at Y$^5$.

Appropriately deuterated intermediate (4), for use in the preparation of compounds of Formula I, Ia, and Ib according to Scheme 1 may be prepared from corresponding deuterated reagents exemplified in Scheme 4.

Scheme 4: Preparation of Intermediate (4)

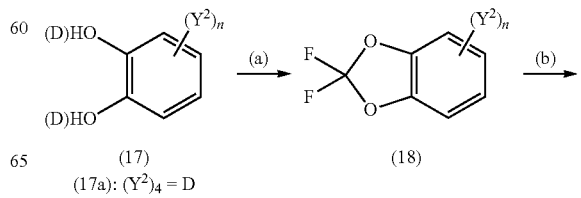

(17a): (Y$^2$)$_4$ = D

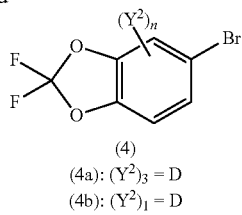

(4)
(4a): $(Y^2)_3 = D$
(4b): $(Y^2)_1 = D$

Reactions and conditions: (a) Thiophosgene, NaH, Bu$_4$N$^+$ •H$_2$F$_3^-$, Iodosuccinimide; (b) TiCl$_4$, HF, Br$_2$ Appropriately deuterated aryl halide (4) is prepared from corresponding deuterated intermediate (18) in a manner analogous to a procedure described in EP 1595877. Intermediate (18) is in turn produced from commercially available catechol-d$_6$ (98 atom % D) or catechol-d$_4$ (96 atom % D) (17a) in a manner analogous to a procedure described by Kuroboshi, M. et al., Synlett, (4), 251-2; 1994. Use of appropriately deuterated reagents allows deuterium incorporation at the $Y^2$ position of a compound of Formula I, Ia, or Ib, or any appropriate intermediate herein, e.g., 90, 95, 97, or 99% deuterium incorporation at any $Y^2$. Intermediate (4b) is prepared as described in US20070191381.

Appropriately deuterated intermediate (7), for use in the preparation of compounds of Formula I, Ia, and Ib according to Scheme 1 may be prepared from corresponding deuterated reagents as described below.

(7a): each $Y^{3a}$ = each $Y^{3b}$ = D
(7b): each $Y^{3a}$ = D; each $Y^{3b}$ = H
(7c): each $Y^{3a}$ = H; each $Y^{3b}$ = D Appropriately deuterated 1-bromo-2-chloroethane-d$_4$ (98 atom % D) (7a) is commercially available, and intermediates (7b) and (7c) are prepared in accordance with a procedure described by Lown, J. et al., Canadian Journal of Chemistry, 59(9), 1347-56; 1981. Use of appropriately deuterated reagents allows deuterium incorporation at the $Y^{3a}$ and $Y^{3b}$ positions of a compound of Formula I, Ia, or Ib, or any appropriate intermediate herein, e.g., 90, 95, 97, or 99% deuterium incorporation at any $Y^{3a}$ or $Y^{3b}$.

Appropriately deuterated intermediate (10), for use in the preparation of compounds of Formula I, Ia, and Ib according to Scheme 1 may be prepared from corresponding deuterated reagents exemplified in Scheme 5.

Scheme 5: Preparation of Intermediate (10)

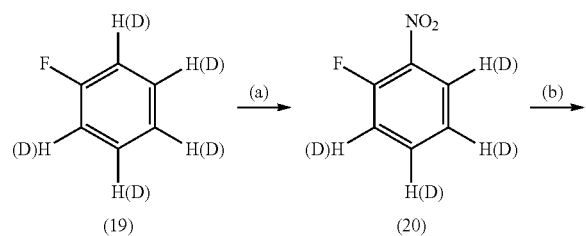

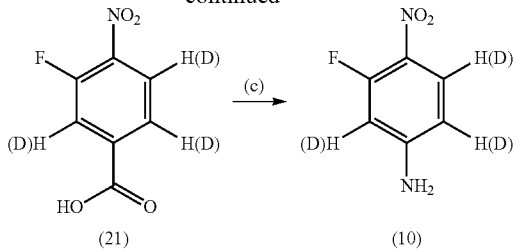

Reactions and conditions: (a) N$_2$O$_5$, Bismuth triflate; (b) methyl 2-chloropropionate, t-BuOK, H$_2$SO$_4$, Na$_2$Cr$_2$O$_7$; (c) t-BuOH, Et$_3$N, DPPA, TFA.

In a manner analogous to a procedure described by Qian, H. et al., Letters in Organic Chemistry, 11(7), 509-512; 2014, bismuth triflate catalyzed nitration of commercially available fluorobenzene-d$_5$ (98 atom % D) (19) provides appropriately deuterated nitrobenzene intermediate (20). Intermediate (20) is then treated with chloropropanoate, followed by chromate oxidation in a manner analogous to a procedure described by Makosza, M. et al., Journal of Organic Chemistry, 67(2), 394-400; 2002, to afford appropriately deuterated benzoic acid intermediate (21). Intermediate (21) is subsequently submitted to standard Curtius reaction in a manner analogous to a procedure described in WO 2004014905 to produce appropriately deuterated aniline intermediate (10). Use of appropriately deuterated reagents allows deuterium incorporation at the $Y^4$ position(s) of a compound of Formula I, Ia, or Ib, or any appropriate intermediate herein, e.g., 90, 95, 97, or 99% deuterium incorporation at any $Y^4$.

Appropriately deuterated intermediate (12), for use in the preparation of compounds of Formula I, Ia, and Ib according to Scheme 1 may be prepared from corresponding deuterated reagents exemplified in Scheme 6.

Scheme 6: Preparation of Intermediate (12)

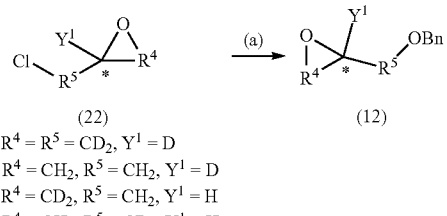

(22a): $R^4 = R^5 = CD_2$, $Y^1 = D$
(22b): $R^4 = CH_2$, $R^5 = CH_2$, $Y^1 = D$
(22c): $R^4 = CD_2$, $R^5 = CH_2$, $Y^1 = H$
(22d): $R^4 = CH_2$, $R^5 = CD_2$, $Y^1 = H$
(22e): $R^4 = CD_2$, $R^5 = CH_2$, $Y^1 = D$
(22f): $R^4 = CH_2$, $R^5 = CD_2$, $Y^1 = D$
(22g): $R^4 = CD_2$, $R^5 = CD_2$, $Y^1 = H$

Reactions and conditions: (a) Benzyl alcohol, NaOH(D), Bu$_4$N$^+$ •Br$^-$, H$_2$O (D$_2$O)

Appropriately deuterated intermediate (12) is prepared from intermediate (22) in a manner analogous to a procedure described by de Almeida, C. et al. Chemical Biology & Drug Design, 78(5), 876-880; 2011. The following deuterated intermediates (22) for use in Scheme 6 are commercially available: Epichlorohydrin-d$_5$ (98 atom % D) (22a), epichlorohydrin-2-d (97 atom % D) (22b), and epichlorohydrin-1,1-d$_2$ (97 atom % D) (22c). Intermediate (22d) is prepared in accordance with a procedure described by Kawakami, Y. et al., Journal of Organic Chemistry, 47(18), 3581-5; 1982; intermediate (22e), according to O'Hagan, D. et al., Journal of Labelled Compounds and Radiopharmaceuticals, 34(9), 871-80; 1994; intermediate (22f), according to a procedure described in WO 2009158010 and intermediate (22g) is prepared in a manner analogous to a procedure described by Ouyang, H. et al., Huaxue Gongye Yu Gongcheng Jishu, 30(6), 4-7; 2009, starting from 1,2,3-propane-1,1,3,3-$d_4$-triol, which is prepared according to a procedure described by Schönewolf, M. et al., (1991), Angew. Chem. Int. Ed. Engl., 30: 183-185. Use of appropriately deuterated reagents allows deuterium incorporation at the $Y^1$, $R^4$ and/or $R^5$ positions of a compound of Formula I, Ia, or Ib, or any appropriate intermediate herein, e.g., 90, 95, 97, or 99% deuterium incorporation at any $Y^1$, $R^4$ and/or $R^5$.

Alternatively, appropriately deuterated chiral epoxide intermediates (12a to 12g)) may be prepared using the Jacobsen's hydrolytic kinetic resolution reaction in a manner analogous to the procedure described by Schaus, S. E. et al., J. Am. Chem. Soc. 2002, 124, 1307.

Appropriately deuterated intermediate (15), for use in the preparation of compounds of Formula I, Ia, and Ib according to Scheme 1 may be prepared from corresponding deuterated reagents exemplified in Scheme 7.

Scheme 7: Preparation of Intermediate (15)

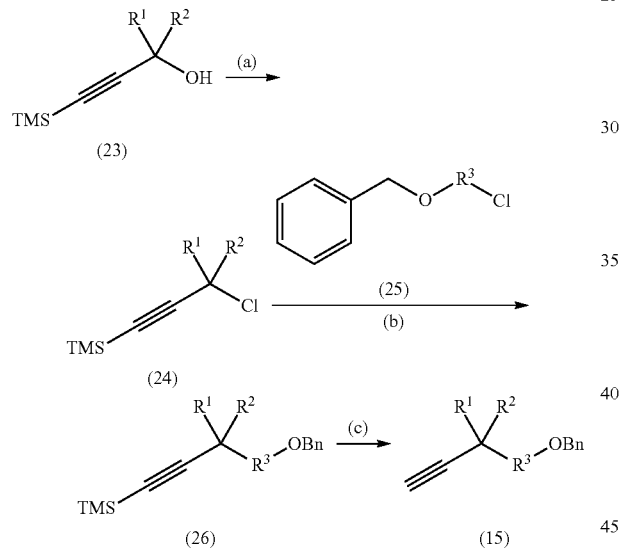

Reactions and conditions: (a) conc. HCl (DCl); (b) Mg; (c) KOH (KOD)

Appropriately deuterated alkyne intermediate (15) is prepared in a manner analogous to the procedure described in WO 2011133751. Thus, appropriately deuterated silyl protected propargyl alcohol intermediate (23) is chlorinated with concentrated HCl to produce appropriately deuterated propargyl chloride intermediate (24). Formation of the Grignard reagent and subsequent nucleophilic substitution with appropropriately deuterated BOM-Cl intermediate (25) produces appropropriately deuterated and silyl protected benzyoxymethyl alkyne intermediate (26). Removal of silyl protection of intermediate (26) with a suitable base such as KOH affords appropriately deuterated benzyoxymethyl alkyne intermediate (15).

Appropriately deuterated intermediate (23), for use in the preparation of compounds of Formula I, Ia, and Ib according to Scheme 1 may be prepared from corresponding deuterated reagents as depicted below.

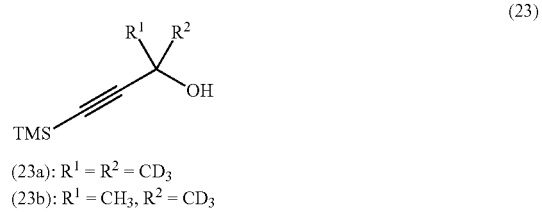

(23a): $R^1 = R^2 = CD_3$
(23b): $R^1 = CH_3$, $R^2 = CD_3$

Appropriately deuterated TMS protected propargyl alcohol intermediate (23) is prepared as described in WO 2011011712, from the following commercially available starting materials: acetone-$d_6$ (99.9 atom % D) (23a), acetone-1,1,1-$d_3$ (99 atom % D) (23b). Use of appropriately deuterated reagents allows deuterium incorporation at the $R^1$ and/or $R^2$ positions of a compound of Formula I, Ia, or Ib, or any appropriate intermediate herein, e.g., 90, 95, 97, or 99% deuterium incorporation at $R^1$ and/or $R^2$.

Appropriately deuterated intermediate (25), for use in the preparation of compounds of Formula I, Ia, and Ib according to Scheme 1 may be prepared from corresponding deuterated exemplified in Scheme 8.

Scheme 8: Preparation of Intermediate (25)

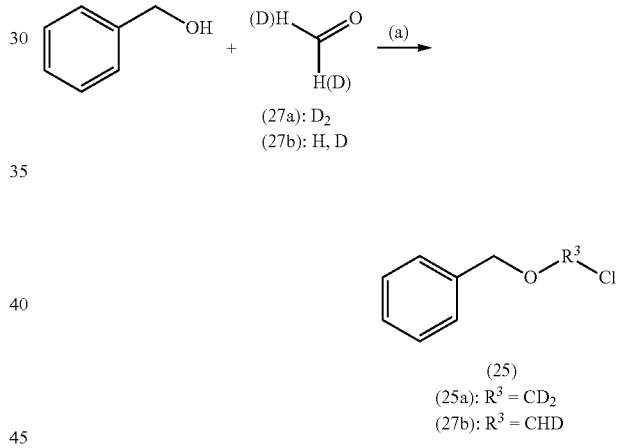

(25a): $R^3 = CD_2$
(27b): $R^3 = CHD$

Appropriately deuterated chloromethylether intermediate (25) is prepared in a manner analogous to a procedure described in CN 102516040. Thus, appropriately deuterated intermediate (25a) is prepared from commercially available formaldehyde-$d_2$ solution (98 atom % D) (27a). Appropriately deuterated intermediate (27b) for use in the preparation of corresponding intermediate (25b) is prepared in accordance with the procedure described by Ouzounian, J. et al., Journal of Labelled Compounds and Radiopharmaceuticals, 23(4), 401-4; 1986. Use of appropriately deuterated reagents allows deuterium incorporation at the $R^3$ position of a compound of Formula I, Ia, or Ib, or any appropriate intermediate herein, e.g., 90, 95, 97, or 99% deuterium incorporation at $R^3$.

Compounds of Formula II, IIa and IIb can be prepared according to the schemes above by substituting intermediate 28 for 1 in Scheme 1. Intermediate 28 can be prepared as shown in Scheme 9 below.

Scheme 9: Preparation of Intermediate (28)

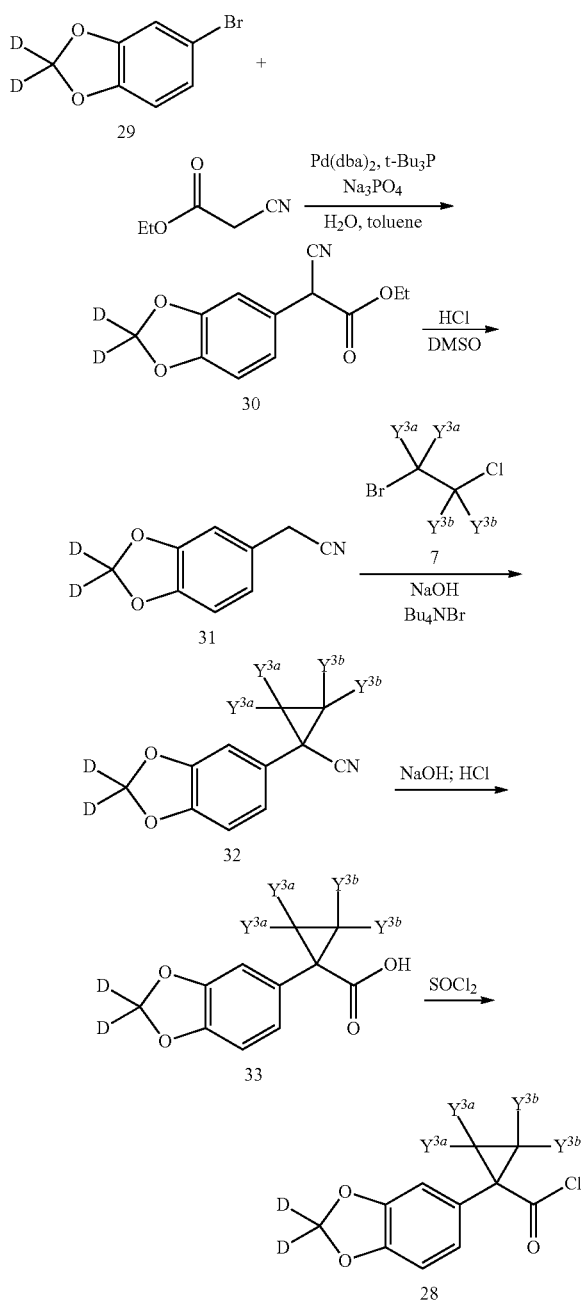

In Scheme 9 above, commercially available 29 is coupled with ethyl cyanoacetate to afford 30. Decarboxylation to 31 followed by alkylation with 7 provides the cyclopropyl intermediate 32. Nitrile hydrolysis, followed by treatment with thionyl chloride, affords 28 which is used instead of 1 in Scheme 1.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula I, Ia and Ib, and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, 4th Ed., John Wiley and Sons (2006); Fieser, L et al., *Fieser and Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pharmaceutical compositions comprising an effective amount of a compound of Formula A, I, Ia, Ib, II, IIa or IIb (e.g., including any of the formulae herein), or a pharmaceutically acceptable salt of said compound; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the subject, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties in the treatment of cystic fibrosis. Such agents include those indicated as being useful in combination with VX-661, including but not limited to, those described in US Patent publication No. US2014/0121208 and US2014/0094499.

Preferably, the second therapeutic agent is an agent useful in the treatment of a disease or condition selected from one or more of a mucolytic agent, bronchodilator, an antibiotic, an anti-infective agent, an anti-inflammatory agent, a CFTR modulator other than a compound of the present invention, a nutritional agent, or an inhibitor of epithelial sodium channel activity.

In some embodiments, the second therapeutic agent is amiloride.

In some embodiments, the second therapeutic agent is ivacaftor.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In some embodiments, an effective amount of a compound of Formula A, I, Ia, Ib, II, IIa or IIb can range from 1 to 500 mg/day. In one aspect of these embodiments, an effective amount of a compound of Formula A, I, Ia, Ib, II, IIa or IIb can range from 5 to 500 mg/day; from 5 to 250 mg/day; from 5 to 200 mg/day; from 5 to 150 mg/day; from 10 to 500 mg/day; from 10 to 250 mg/day; from 10 to 200 mg/day; and from 10 to 150 mg/day. Other effective amounts range from 1 to 10 mg/day; from 1 to 30 mg/day; from 1 to 100 mg/day; from 1 to 150 mg/day; from 10 to 30 mg/day; from 10 to 100 mg/day; from 10 to 150 mg/day; from 30 to 100 mg/day; from 30 to 150 mg/day; and from 100 to 150 mg/day.

Effective dosage amount may be administered as a single dose once a day, or as split doses administered two, three or four times a day.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician. For example, guidance for selecting an effective dose can be determined by reference to the prescribing information for VX-661.

For pharmaceutical compositions that comprise a second therapeutic agent (such as ivacaftor), an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to other embodiments, the invention provides a method of treating a CFTR-mediated disease, comprising the step of administering to the subject an effective amount of a compound or a composition of this invention. In one aspect of these embodiments the subject is a patient in need of such treatment.

A "CFTR-mediated disease" is a disease or condition that is associated with a defect in the cystic fibrosis transmembrane conductance regulator and includes, but is not limited to, a disease or disorder selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, protein C deficiency, Type 1 hereditary angioedema, lipid processing deficiencies, familial hypercholesterolemia, Type 1 chylomicronemia, abetalipoproteinemia, lysosomal storage diseases, 1-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases, Alzheimer's disease, Parkinson's disease, amyotrophic lateral sclerosis, progressive supranuclear palsy, Pick's disease, several polyglutamine neurological disorders, Huntington's, spinocerebellar ataxia type I, spinal and bulbar muscular atrophy, dentatorubral pallidoluysian, myotonic dystrophy, spongiform encephalopathies, hereditary Creutzfeldt-Jakob disease (due to prion protein processing defect), Fabry disease, Straussler-Scheinker syndrome, COPD, dry-eye disease, Sjogren's disease, Osteoporosis, Osteopenia, Gorham's Syndrome, chloride channelopathies, myotonia congenita (Thomson and Becker forms), Bartter's syndrome type III, Dent's disease, hyperexplexia, epilepsy, lysosomal storage disease, Angelman syndrome, Primary Ciliary Dyskinesia (PCD), inherited disorders of the structure and/or function of cilia, PCD with situs inversus (also known as Kartagener syndrome), PCD without situs inversus, or ciliary aplasia.

In specific embodiments, the method of this invention is used to treat cystic fibrosis in a subject in need thereof. In one aspect of these embodiments, the cystic fibrosis is characterized by the presence at least one copy of a ΔF508 CFTR mutation. In a more specific aspect of these embodiments, the subject has one copy of a ΔF508 CFTR mutation and one copy of a G551D CFTR mutation. In another more specific aspect of these embodiments, the subject is homozygous for the ΔF508 CFTR mutation.

Identifying a subject in need of such treatment can be in the judgment of a subject or a health care professional and can be subjective (e.g. opinion) or objective (e.g. measurable by a test or diagnostic method).

In another embodiment, any of the above methods of treatment comprises the further step of co-administering to the subject in need thereof one or more second therapeutic agents. The choice of second therapeutic agent may be made from any second therapeutic agents set forth above for use in combination compositions comprising a compound of this invention and a second therapeutic agent.

In one particular aspect, the combination therapies of this invention include co-administering a compound of Formula A, I, Ia, Ib, II, IIa or IIb and amiloride.

In another particular aspect, the combination therapies of this invention include co-administering a compound of Formula A, I, Ia, Ib, II, IIa or IIb and ivacaftor. In certain embodiments, the effective amount of ivacaftor administered in combination with the compound of Formula A, I, Ia, Ib, II, IIa or IIb can range from 1 to 500 mg/day. In one aspect of these embodiments, an effective amount of ivacaftor can range from 5 to 500 mg/day; from 5 to 250 mg/day; from 5 to 200 mg/day; from 5 to 150 mg/day; from 10 to 500 mg/day; from 10 to 250 mg/day; from 10 to 200 mg/day; and from 10 to 150 mg/day. Other effective amounts range from 1 to 10 mg/day; from 1 to 30 mg/day; from 1 to 100 mg/day; from 1 to 150 mg/day; from 10 to 30 mg/day; from 10 to 100 mg/day; from 10 to 150 mg/day; from 30 to 100 mg/day; from 30 to 150 mg/day; and from 100 to 150 mg/day.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula A, I, Ia, Ib, II, IIa or IIb alone or together with one or more of the above-described second therapeutic agents in the manufacture of a medicament, either as a single composition or as separate dosage forms, for treatment in a subject of a disease, disorder or symptom set forth above. Another aspect of the invention is a compound of Formula A, I, Ia, Ib, II, IIa or IIb for use in the treatment in a subject of a disease, disorder or symptom thereof delineated herein.

EXAMPLE 1.

Evaluation of Metabolic Stability

Microsomal Assay: Human liver microsomes (20 mg/mL) are obtained from Xenotech, LLC (Lenexa, Kans.). β-nicotinamide adenine dinucleotide phosphate, reduced form (NADPH), magnesium chloride ($MgCl_2$), and dimethyl sulfoxide (DMSO) are purchased from Sigma-Aldrich.

Determination of Metabolic Stability: 7.5 mM stock solutions of test compounds are prepared in DMSO. The 7.5 mM stock solutions are diluted to 12.5-50 µM in acetonitrile (ACN). The 20 mg/mL human liver microsomes are diluted to 0.625 mg/mL in 0.1 M potassium phosphate buffer, pH 7.4, containing 3 mM $MgCl_2$. The diluted microsomes are added to wells of a 96-well deep-well polypropylene plate in triplicate. A 10 µL aliquot of the 12.5-50 µM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 µM test compound, and 2 mM NADPH in 0.1 M potassium phosphate buffer, pH 7.4, and 3 mM $MgCl_2$. The reaction mixtures are incubated at 37° C., and 50 µL aliquots are removed at 0, 5, 10, 20, and 30 minutes and added to shallow-well 96-well plates which contain 50 µL of ice-cold ACN with internal standard to stop the reactions. The plates are stored at 4° C. for 20 minutes after which 100 µL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for the non-deuterated counterpart of the compound of Formula A, I, Ia, Ib, II, IIa or IIb and the positive control, 7-ethoxycoumarin (1 µM). Testing is done in triplicate.

Data Analysis: The in vitro $t_{1/2s}$ for test compounds are calculated from the slopes of the linear regression of % parent remaining (ln) vs incubation time relationship.

in vitro $t_{1/2}=0.693/k$ $k$=−[slope of linear regression of % parent remaining (ln) vs incubation time]

Data analysis is performed using Microsoft Excel Software.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

We claim:
1. A compound of Formula A:

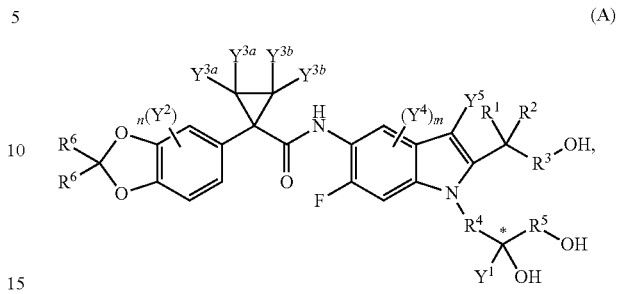

(A)

or a pharmaceutically acceptable salt thereof, wherein:
each of $R^1$ and $R^2$ is independently selected from —$CH_3$, —$CH_2D$, —$CHD_2$, and —$CD_3$;
each of $R^3$, $R^4$ and $R^5$ is independently selected from —$CH_2$—, —CHD- and —$CD_2$-;
each $R^6$ is independently fluorine or deuterium;
$Y^1$ is selected from hydrogen and deuterium;
each $Y^{3a}$ and each $Y^{3b}$ is selected from hydrogen and deuterium;
$Y^5$ is selected from hydrogen and deuterium;
each of $Y^2$ and $Y^4$, if present, is deuterium;
n is 0, 1, 2, or 3;
m is 0, 1, or 2; and
when $R^1$ and $R^2$ are each —$CH_3$; $R^4$, and $R^5$ are each —$CH_2$-; each $R^6$ is fluorine; each $Y^{3a}$ and each $Y^{3b}$ is hydrogen; each of $Y^1$ and $Y^5$ is hydrogen; and each of m and n is 0; then $R^3$ is either —CHD- or —$CH_2$-.

2. The compound of claim 1 wherein the compound is a compound of Formula Ib:

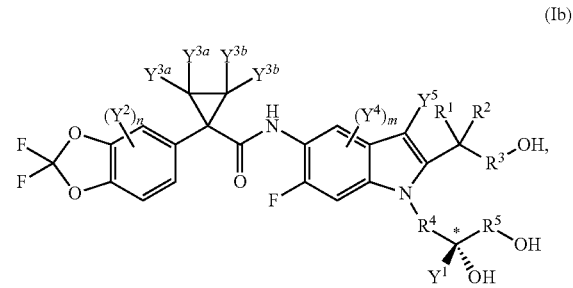

(Ib)

or a pharmaceutically acceptable salt thereof, wherein:
each of $R^1$ and $R^2$ is independently selected from —$CH_3$, —$CH_2D$, —$CHD_2$, and —$CD_3$;
each of $R^3$, $R^4$ and $R^5$ is independently selected from —$CH_2$—, —CHD- and —$CD_2$-;
$Y^1$ is selected from hydrogen and deuterium;
each $Y^{3a}$ and each $Y^{3b}$ is selected from hydrogen and deuterium;
$Y^5$ is selected from hydrogen and deuterium;
each of $Y^2$ and $Y^4$, if present, is deuterium;
n is 0, 1, 2, or 3;
m is 0, 1, or 2; and
when $R^1$ and $R^2$ are each —$CH_3$; $R^4$, and $R^5$ are each —$CH_2$—; each $Y^{3a}$ and each $Y^{3b}$ is hydrogen; each of $Y^1$ and $Y^5$ is hydrogen; and each of m and n is 0; then $R^3$ is either —CHD- or —$CD_2$-.

3. The compound of claim 1 wherein the compound is a compound of Formula IIb:

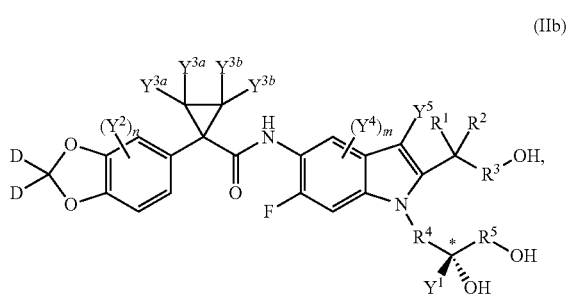

(IIb)

or a pharmaceutically acceptable salt thereof, wherein:
each of $R^1$ and $R^2$ is independently selected from —CH$_3$, —CH$_2$D, —CHD$_2$, and —CD$_3$;
each of $R^3$, $R^4$ and $R^5$ is independently selected from —CH$_2$—, —CHD- and —CD$_2$-;
$Y^1$ is selected from hydrogen and deuterium;
each $Y^{3a}$ and each $Y^{3b}$ is selected from hydrogen and deuterium;
$Y^5$ is selected from hydrogen and deuterium;
each of $Y^2$ and $Y^4$, if present, is deuterium;
n is 0, 1, 2, or 3; and
m is 0, 1, or 2.

4. The compound of claim 1, wherein;
each of $R^1$ and $R^2$ is independently selected from —CH$_3$ and —CD$_3$;
each of $R^3$, $R^4$ and $R^5$ is independently selected from —CH$_2$— and —CD$_2$-;
each $Y^{3a}$ is the same and each $Y^{3b}$ is the same;
n is 0 or 3; and
m is 0 or 2.

5. The compound of claim 1 wherein $R^1$ and $R^2$ are the same.

6. The compound of claim 5, wherein $R^1$ and $R^2$ are —CH$_3$.

7. The compound of claim 5, wherein $R^1$ and $R^2$ are —CD$_3$.

8. The compound of claim 1, wherein $R^3$ is —CH$_2$—.

9. The compound of claim 1, wherein $R^3$ is —CD$_2$-.

10. The compound of claim 1, wherein $R^4$ is —CH$_2$— and $R^5$ is —CD$_2$-.

11. The compound of claim 1, wherein $R^4$ is —CD$_2$- and $R^5$ is —CH$_2$—.

12. The compound of claim 1, wherein $R^4$ is —CD$_2$- and $R^5$ is —CD$_2$-.

13. The compound of claim 1, wherein $R^4$ is —CH$_2$— and $R^5$ is —CH$_2$—.

14. The compound of claim 1, wherein $Y^1$ is deuterium.

15. The compound of claim 1, wherein $Y^1$ is hydrogen.

16. The compound of claim 1, wherein each $Y^{3a}$ is deuterium and each $Y^{3b}$ is hydrogen.

17. The compound of claim 1, wherein each $Y^{3a}$ is hydrogen and each $Y^{3b}$ is deuterium.

18. The compound of claim 1, wherein each $Y^{3a}$ is deuterium and each $Y^{3b}$ is deuterium.

19. The compound of claim 1, wherein each $Y^{3a}$ is hydrogen and each $Y^{3b}$ is hydrogen.

20. The compound of claim 1, wherein any atom not designated as deuterium is present at its natural isotopic abundance.

21. The compound of claim 2, wherein $R^1$ and $R^2$ are the same; each of n and m is 0; $Y^5$ is hydrogen; and each $Y^{3a}$ and $Y^{3b}$ is hydrogen, wherein the compound is selected from any one of the compounds set forth in the table below:

| Compound # | $R^1/R^2$ | $R^3$ | $R^4$ | $R^5$ | $Y^1$ |
|---|---|---|---|---|---|
| 100b | CD$_3$ | CD$_2$ | CD$_2$ | CH$_2$ | H |
| 101b | CD$_3$ | CD$_2$ | CD$_2$ | CD$_2$ | H |
| 102b | CD$_3$ | CD$_2$ | CH$_2$ | CH$_2$ | H |
| 103b | CD$_3$ | CD$_2$ | CH$_2$ | CD$_2$ | H |
| 104b | CD$_3$ | CD$_2$ | CD$_2$ | CH$_2$ | D |
| 105b | CD$_3$ | CD$_2$ | CD$_2$ | CD$_2$ | D |
| 106b | CD$_3$ | CD$_2$ | CH$_2$ | CH$_2$ | D |
| 107b | CD$_3$ | CD$_2$ | CH$_2$ | CD$_2$ | D |
| 108b | CH$_3$ | CH$_2$ | CD$_2$ | CH$_2$ | H |
| 109b | CH$_3$ | CH$_2$ | CD$_2$ | CD$_2$ | H |
| 110b | CH$_3$ | CH$_2$ | CH$_2$ | CD$_2$ | H |
| 111b | CH$_3$ | CH$_2$ | CD$_2$ | CH$_2$ | D |
| 112b | CH$_3$ | CH$_2$ | CD$_2$ | CD$_2$ | D |
| 113b | CH$_3$ | CH$_2$ | CH$_2$ | CH$_2$ | D |
| 114b | CH$_3$ | CH$_2$ | CH$_2$ | CD$_2$ | D |
| 115b | CD$_3$ | CH$_2$ | CD$_2$ | CH$_2$ | H |
| 116b | CD$_3$ | CH$_2$ | CD$_2$ | CD$_2$ | H |
| 117b | CD$_3$ | CH$_2$ | CH$_2$ | CH$_2$ | H |
| 118b | CD$_3$ | CH$_2$ | CH$_2$ | CD$_2$ | H |
| 119b | CD$_3$ | CH$_2$ | CD$_2$ | CD$_2$ | D |
| 120b | CD$_3$ | CH$_2$ | CD$_2$ | CH$_2$ | D |
| 121b | CD$_3$ | CH$_2$ | CH$_2$ | CH$_2$ | D |
| 122b | CD$_3$ | CH$_2$ | CH$_2$ | CD$_2$ | D |
| 123b | CH$_3$ | CD$_2$ | CD$_2$ | CH$_2$ | H |
| 124b | CH$_3$ | CD$_2$ | CD$_2$ | CD$_2$ | H |
| 125b | CH$_3$ | CD$_2$ | CH$_2$ | CD$_2$ | H |
| 126b | CH$_3$ | CD$_2$ | CH$_2$ | CH$_2$ | H |
| 127b | CH$_3$ | CD$_2$ | CD$_2$ | CH$_2$ | D |
| 128b | CH$_3$ | CD$_2$ | CD$_2$ | CD$_2$ | D |
| 129b | CH$_3$ | CD$_2$ | CH$_2$ | CH$_2$ | D |
| 130b | CH$_3$ | CD$_2$ | CH$_2$ | CD$_2$ | D | or a pharmaceutically acceptable salt thereof, wherein any atom not designated as deuterium is present at its natural isotopic abundance.

22. The compound of claim 3, wherein $R^1$ and $R^2$ are the same; each of n and m is 0; $Y^5$ is hydrogen; and each $Y^{3a}$ and $Y^{3b}$ is hydrogen, wherein the compound is selected from any one of the compounds set forth in the table below:

| Compound # | $R^1/R^2$ | $R^3$ | $R^4$ | $R^5$ | $Y^1$ |
|---|---|---|---|---|---|
| 300b | CD$_3$ | CD$_2$ | CD$_2$ | CH$_2$ | H |
| 301b | CD$_3$ | CD$_2$ | CD$_2$ | CD$_2$ | H |
| 302b | CD$_3$ | CD$_2$ | CH$_2$ | CH$_2$ | H |
| 303b | CD$_3$ | CD$_2$ | CH$_2$ | CD$_2$ | H |
| 304b | CD$_3$ | CD$_2$ | CD$_2$ | CH$_2$ | D |
| 305b | CD$_3$ | CD$_2$ | CD$_2$ | CD$_2$ | D |
| 306b | CD$_3$ | CD$_2$ | CH$_2$ | CH$_2$ | D |
| 307b | CD$_3$ | CD$_2$ | CH$_2$ | CD$_2$ | D |
| 308b | CH$_3$ | CH$_2$ | CD$_2$ | CH$_2$ | H |
| 309b | CH$_3$ | CH$_2$ | CD$_2$ | CD$_2$ | H |
| 310b | CH$_3$ | CH$_2$ | CH$_2$ | CD$_2$ | H |
| 311b | CH$_3$ | CH$_2$ | CD$_2$ | CH$_2$ | D |
| 312b | CH$_3$ | CH$_2$ | CD$_2$ | CD$_2$ | D |
| 313b | CH$_3$ | CH$_2$ | CH$_2$ | CH$_2$ | D |
| 314b | CH$_3$ | CH$_2$ | CH$_2$ | CD$_2$ | D |
| 315b | CD$_3$ | CH$_2$ | CD$_2$ | CH$_2$ | H |
| 316b | CD$_3$ | CH$_2$ | CD$_2$ | CD$_2$ | H |
| 317b | CD$_3$ | CH$_2$ | CH$_2$ | CH$_2$ | H |
| 318b | CD$_3$ | CH$_2$ | CH$_2$ | CD$_2$ | H |
| 319b | CD$_3$ | CH$_2$ | CD$_2$ | CD$_2$ | D |
| 320b | CD$_3$ | CH$_2$ | CD$_2$ | CH$_2$ | D |
| 321b | CD$_3$ | CH$_2$ | CH$_2$ | CH$_2$ | D |
| 322b | CD$_3$ | CH$_2$ | CH$_2$ | CD$_2$ | D |
| 323b | CH$_3$ | CD$_2$ | CD$_2$ | CH$_2$ | H |
| 324b | CH$_3$ | CD$_2$ | CD$_2$ | CD$_2$ | H |
| 325b | CH$_3$ | CD$_2$ | CH$_2$ | CD$_2$ | H |
| 326b | CH$_3$ | CD$_2$ | CH$_2$ | CH$_2$ | H |
| 327b | CH$_3$ | CD$_2$ | CD$_2$ | CH$_2$ | D |
| 328b | CH$_3$ | CD$_2$ | CD$_2$ | CD$_2$ | D |
| 329b | CH$_3$ | CD$_2$ | CH$_2$ | CH$_2$ | D |
| 330b | CH$_3$ | CD$_2$ | CH$_2$ | CD$_2$ | D |
| 331b | CH$_3$ | CH$_2$ | CH$_2$ | CH$_2$ | H | or a pharmaceutically acceptable salt thereof, wherein any atom not designated as deuterium is present at its natural isotopic abundance.

23. The compound of claim 2, wherein $R^1$ and $R^2$ are the same; each of n and m is 0; $Y^5$ is hydrogen; and each $Y^{3a}$ and $Y^{3b}$ is deuterium, wherein the compound is selected from any one of the compounds set forth in the table below:

| Compound # | $R^1/R^2$ | $R^3$ | $R^4$ | $R^5$ | $Y^1$ |
|---|---|---|---|---|---|
| 200b | $CD_3$ | $CD_2$ | $CD_2$ | $CH_2$ | H |
| 201b | $CD_3$ | $CD_2$ | $CD_2$ | $CD_2$ | H |
| 202b | $CD_3$ | $CD_2$ | $CH_2$ | $CH_2$ | H |
| 203b | $CD_3$ | $CD_2$ | $CH_2$ | $CD_2$ | H |
| 204b | $CD_3$ | $CD_2$ | $CD_2$ | $CH_2$ | D |
| 205b | $CD_3$ | $CD_2$ | $CD_2$ | $CD_2$ | D |
| 206b | $CD_3$ | $CD_2$ | $CH_2$ | $CH_2$ | D |
| 207b | $CD_3$ | $CD_2$ | $CH_2$ | $CD_2$ | D |
| 208b | $CH_3$ | $CH_2$ | $CD_2$ | $CH_2$ | H |
| 209b | $CH_3$ | $CH_2$ | $CD_2$ | $CD_2$ | H |
| 210b | $CH_3$ | $CH_2$ | $CH_2$ | $CD_2$ | H |
| 211b | $CH_3$ | $CH_2$ | $CH_2$ | $CH_2$ | D |
| 212b | $CH_3$ | $CH_2$ | $CD_2$ | $CH_2$ | D |
| 213b | $CH_3$ | $CH_2$ | $CD_2$ | $CD_2$ | D |
| 214b | $CH_3$ | $CH_2$ | $CH_2$ | $CD_2$ | D |
| 215b | $CD_3$ | $CH_2$ | $CH_2$ | $CH_2$ | H |
| 216b | $CD_3$ | $CH_2$ | $CD_2$ | $CH_2$ | H |
| 217b | $CD_3$ | $CH_2$ | $CH_2$ | $CH_2$ | H |
| 218b | $CD_3$ | $CH_2$ | $CH_2$ | $CH_2$ | H |
| 219b | $CD_3$ | $CH_2$ | $CH_2$ | $CD_2$ | D |
| 220b | $CD_3$ | $CH_2$ | $CD_2$ | $CH_2$ | D |
| 221b | $CD_3$ | $CH_2$ | $CH_2$ | $CD_2$ | D |
| 222b | $CD_3$ | $CH_2$ | $CH_2$ | $CH_2$ | D |
| 223b | $CH_3$ | $CD_2$ | $CD_2$ | $CH_2$ | H |
| 224b | $CH_3$ | $CD_2$ | $CD_2$ | $CD_2$ | H |
| 225b | $CH_3$ | $CD_2$ | $CH_2$ | $CD_2$ | H |
| 226b | $CH_3$ | $CD_2$ | $CH_2$ | $CH_2$ | H |
| 227b | $CH_3$ | $CD_2$ | $CD_2$ | $CH_2$ | D |
| 228b | $CH_3$ | $CD_2$ | $CD_2$ | $CD_2$ | D |
| 229b | $CH_3$ | $CD_2$ | $CH_2$ | $CD_2$ | D |
| 230b | $CH_3$ | $CD_2$ | $CH_2$ | $CH_2$ | D |
| 231b | $CH_3$ | $CH_2$ | $CH_2$ | $CH_2$ | H | or a pharmaceutically acceptable salt thereof, wherein any atom not designated as deuterium is present at its natural isotopic abundance.

24. The compound of claim 3, wherein $R^1$ and $R^2$ are the same; each of n and m is 0; $Y^5$ is hydrogen; and each $Y^{3a}$ and $Y^{3b}$ is deuterium, wherein the compound is selected from any one of the compounds set forth in the table below:

| Compound # | $R^1/R^2$ | $R^3$ | $R^4$ | $R^5$ | $Y^1$ |
|---|---|---|---|---|---|
| 400b | $CD_3$ | $CD_2$ | $CD_2$ | $CH_2$ | H |
| 401b | $CD_3$ | $CD_2$ | $CD_2$ | $CD_2$ | H |
| 402b | $CD_3$ | $CD_2$ | $CH_2$ | $CH_2$ | H |
| 403b | $CD_3$ | $CD_2$ | $CH_2$ | $CD_2$ | H |
| 404b | $CD_3$ | $CD_2$ | $CD_2$ | $CH_2$ | D |
| 405b | $CD_3$ | $CD_2$ | $CD_2$ | $CD_2$ | D |
| 406b | $CD_3$ | $CD_2$ | $CH_2$ | $CH_2$ | D |
| 407b | $CD_3$ | $CD_2$ | $CH_2$ | $CD_2$ | D |
| 408b | $CH_3$ | $CH_2$ | $CD_2$ | $CH_2$ | H |
| 409b | $CH_3$ | $CH_2$ | $CD_2$ | $CD_2$ | H |
| 410b | $CH_3$ | $CH_2$ | $CH_2$ | $CD_2$ | H |
| 411b | $CH_3$ | $CH_2$ | $CH_2$ | $CH_2$ | D |
| 412b | $CH_3$ | $CH_2$ | $CD_2$ | $CH_2$ | D |
| 413b | $CH_3$ | $CH_2$ | $CD_2$ | $CD_2$ | D |
| 414b | $CH_3$ | $CH_2$ | $CH_2$ | $CD_2$ | D |
| 415b | $CD_3$ | $CH_2$ | $CH_2$ | $CH_2$ | H |
| 416b | $CD_3$ | $CH_2$ | $CD_2$ | $CH_2$ | H |
| 417b | $CD_3$ | $CH_2$ | $CH_2$ | $CH_2$ | H |
| 418b | $CD_3$ | $CH_2$ | $CH_2$ | $CH_2$ | H |
| 419b | $CD_3$ | $CH_2$ | $CH_2$ | $CD_2$ | D |
| 420b | $CD_3$ | $CH_2$ | $CD_2$ | $CH_2$ | D |
| 421b | $CD_3$ | $CH_2$ | $CH_2$ | $CH_2$ | D |
| 422b | $CD_3$ | $CH_2$ | $CH_2$ | $CD_2$ | D |
| 423b | $CH_3$ | $CD_2$ | $CD_2$ | $CH_2$ | H |
| 424b | $CH_3$ | $CD_2$ | $CD_2$ | $CD_2$ | H |
| 425b | $CH_3$ | $CD_2$ | $CH_2$ | $CD_2$ | H |
| 426b | $CH_3$ | $CD_2$ | $CH_2$ | $CH_2$ | H |
| 427b | $CH_3$ | $CD_2$ | $CD_2$ | $CH_2$ | D |
| 428b | $CH_3$ | $CD_2$ | $CD_2$ | $CD_2$ | D |
| 429b | $CH_3$ | $CD_2$ | $CH_2$ | $CH_2$ | D |
| 430b | $CH_3$ | $CD_2$ | $CH_2$ | $CD_2$ | D |
| 431b | $CH_3$ | $CH_2$ | $CH_2$ | $CH_2$ | H | or a pharmaceutically acceptable salt thereof, wherein any atom not designated as deuterium is present at its natural isotopic abundance.

25. A compound selected from any one of the following:

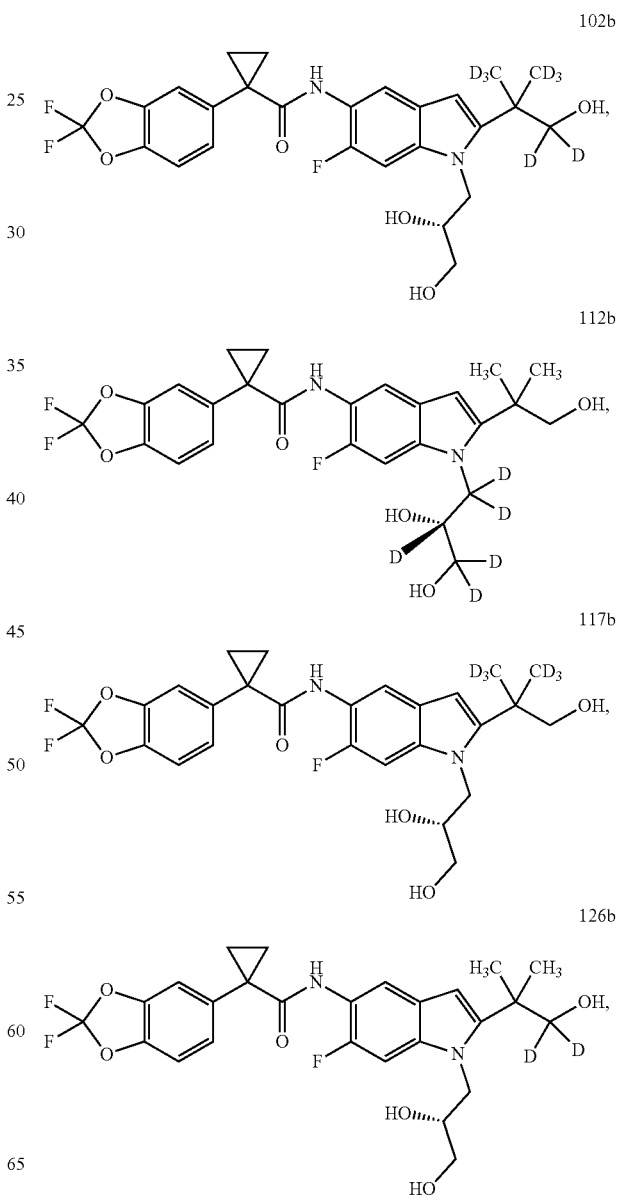

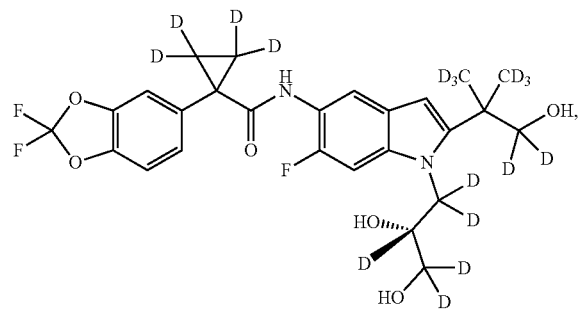

205b

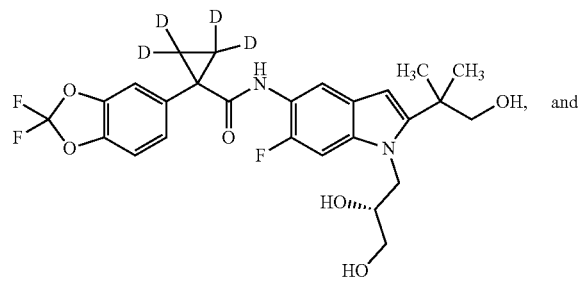

231b

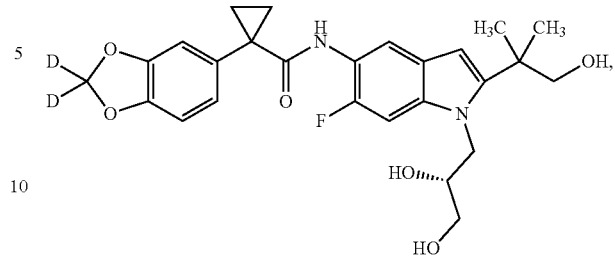

331b or a pharmaceutically acceptable salt thereof, wherein any atom not designated as deuterium is present at its natural isotopic abundance.

26. A pharmaceutical composition comprising a compound of claim 1 and a pharmaceutically acceptable carrier.

27. A method of treating cystic fibrosis in a subject characterized by the presence of at least one copy of a ΔF508 CFTR mutation comprising the step of administering to the subject in need thereof a composition of claim 26.

28. The method of claim 27, wherein the subject is homozygous for the ΔF508 CFTR mutation.

29. The method of claim 27, wherein the subject has one copy of the ΔF508 CFTR mutation and one copy of a G551D CFTR mutation.

\* \* \* \* \*

UNITED STATES PATENT AND TRADEMARK OFFICE
CERTIFICATE OF CORRECTION

PATENT NO. : 10,196,384 B2
APPLICATION NO. : 15/562860
DATED : February 5, 2019
INVENTOR(S) : I. Robert Silverman et al.

It is certified that error appears in the above-identified patent and that said Letters Patent is hereby corrected as shown below:

In the Claims

Claim 1, Column 42, Line 33, "then $R^3$ is either --CHD- or --CH$_2$-." should read -- then $R^3$ is either --CHD- or --CD$_2$-. --.

Claim 4, Column 43, Line 27, "The compound of claim 1, wherein;" should read -- The compound of claim 1, wherein: --.

Signed and Sealed this
Twenty-first Day of May, 2019

Andrei Iancu
*Director of the United States Patent and Trademark Office*